(12) United States Patent
Hubbard et al.

(10) Patent No.: US 11,676,438 B2
(45) Date of Patent: Jun. 13, 2023

(54) AUTHENTICATION AND AGE VERIFICATION FOR AN AEROSOL DELIVERY DEVICE

(71) Applicant: RAI Strategic Holdings, Inc., Winston-Salem, NC (US)

(72) Inventors: Sawyer Hubbard, Winston-Salem, NC (US); Leigh Ann Joyce, Winston-Salem, NC (US); Jared Aller, Winston-Salem, NC (US); Jake Novak, Winston-Salem, NC (US); Sean Daugherty, Winston-Salem, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 967 days.

(21) Appl. No.: 16/415,460

(22) Filed: May 17, 2019

(65) Prior Publication Data
US 2020/0315259 A1    Oct. 8, 2020

Related U.S. Application Data

(60) Provisional application No. 62/828,222, filed on Apr. 2, 2019.

(51) Int. Cl.
*G07C 9/32* (2020.01)
*H04L 9/40* (2022.01)
*H02J 7/00* (2006.01)

(52) U.S. Cl.
CPC .............. *G07C 9/32* (2020.01); *H02J 7/0042* (2013.01); *H04L 63/08* (2013.01); *H02J 7/00045* (2020.01)

(58) Field of Classification Search
CPC .. H04W 4/14; H04W 4/12; G07C 9/32; H02J 7/0042; H02J 7/00045; H04L 63/08; A24F 40/60; A24F 40/65; A24F 40/50
See application file for complete search history.

(56) References Cited

U.S. PATENT DOCUMENTS

| | | | |
|---|---|---|---|
| 2014/0120961 A1* | 5/2014 | Buck | G06F 1/329 455/466 |
| 2015/0181945 A1 | 7/2015 | Tremblay | |

(Continued)

FOREIGN PATENT DOCUMENTS

| | | |
|---|---|---|
| GB | 2522395 A | 7/2015 |
| JP | 2018527890 A | 9/2018 |

(Continued)

OTHER PUBLICATIONS

Office Action from Canadian Application No. 3135789 dated Dec. 7, 2021, all pages cited in its entirety.

(Continued)

*Primary Examiner* — Wei Zhao
(74) *Attorney, Agent, or Firm* — Burr & Forman LLP

(57) ABSTRACT

A charger for an electronic nicotine delivery systems ("ENDS") device, which may include aerosol delivery devices provides functionality for authentication, including age verification. Such devices may be restricted based on age or other factors that require some form of authentication, verification, and/or identification to satisfy the restriction. The accessory or charger may provide or connect with a verification system for confirming an age of a user. If the authentication or verification is not satisfied, the charger or accessory will not charge the device, rendering it unusable.

23 Claims, 16 Drawing Sheets

(56) References Cited

U.S. PATENT DOCUMENTS

| | | | |
|---|---|---|---|
| 2016/0087314 A1 | 3/2016 | Arashima et al. | |
| 2016/0143361 A1 * | 5/2016 | Juster et al. | |
| 2017/0346635 A1 * | 11/2017 | Gummeson | ............... G06F 1/16 |
| 2018/0020441 A1 * | 1/2018 | Lo | ......................... H04W 76/14 |
| 2018/0020720 A1 | 1/2018 | Matischek et al. | |
| 2020/0352249 A1 * | 11/2020 | Achtien | ............ A61M 15/0066 |

FOREIGN PATENT DOCUMENTS

| | | |
|---|---|---|
| JP | 2019500006 A | 1/2019 |
| RU | 2651475 C2 | 4/2018 |
| RU | 2666100 C2 | 9/2018 |
| RU | 2678437 C1 | 1/2019 |

OTHER PUBLICATIONS

Korean Office Action dated Mar. 21, 2022 in corresponding Korean Application No. 10-2021-7035624 filed Nov. 1, 2021.

Notice of Decision for Rejection issued in corresponding Korean Application No. 10-2021-7035624 dated Aug. 24, 2022, all enclosed pages cited.

Notification of Results of the Patentability Test of the invention issued in corresponding Russian Application No. 2021131888 dated Mar. 24, 2022, all enclosed pages cited.

Office Action issued in corresponding Japanese Application No. 2021-560479 dated Jun. 14, 2022, all enclosed pages cited.

Office Action issued in corresponding Canadian Application No. 3,135,789 dated Jul. 20, 2022, all enclosed pages cited.

Notice of Allowance issued in corresponding Japanese Application No. 2021-560479 dated Oct. 11, 2022, all enclosed pages cited.

* cited by examiner

AUTHENTICATION AND AGE VERIFICATION FOR AN AEROSOL DELIVERY DEVICE

PRIORITY CLAIM

This application claims priority to U.S. Provisional App. No. 62/828,222, filed on Apr. 2, 2019, entitled "AUTHENTICATION AND AGE VERIFICATION FOR AN AEROSOL DELIVERY DEVICE," the entire disclosure of which is hereby incorporated by reference.

TECHNOLOGICAL FIELD

The present disclosure relates to an accessory, such as a charger for an electronic nicotine delivery systems ("ENDS") device, including aerosol delivery devices such as smoking articles that produce aerosol. The charger accessory provides functionality for authentication of a user, including age verification.

BACKGROUND

Many devices have been proposed through the years as improvements upon, or alternatives to, smoking products that require combusting tobacco for use. Some example alternatives have included devices wherein a solid or liquid fuel is combusted to transfer heat to tobacco or wherein a chemical reaction is used to provide such heat source. Additional example alternatives use electrical energy to heat tobacco and/or other aerosol generating substrate materials, such as described in U.S. Pat. No. 9,078,473 to Worm et al., which is incorporated herein by reference. Generally, a device using electrical energy to heat tobacco or other substances may be referred to as an electronic nicotine delivery systems ("ENDS") device.

Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous alternative smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0096781 to Sears et al., U.S. Pat. App. Pub. No. 2014/0096782 to Ampolini et al., U.S. Pat. App. Pub. No. 2015/0059780 to Davis et al., and U.S. patent application Ser. No. 15/222,615 to Watson et al., filed Jul. 28, 2016, all of which are incorporated herein by reference. See also, for example, the various implementations of products and heating configurations described in the background sections of U.S. Pat. No. 5,388,594 to Counts et al. and U.S. Pat. No. 8,079,371 to Robinson et al., which are incorporated by reference.

The smoking articles described above may be subject to certain restrictions, including age restrictions. In some countries, use of the articles is limited based on user age. An improved age verification process is needed to confirm compliance with the restrictions.

BRIEF SUMMARY

The present disclosure relates to an accessory, such as a charger for an electronic nicotine delivery systems ("ENDS") device, which may include aerosol delivery devices such as smoking articles that produce aerosol. The ENDS or aerosol delivery devices require some form of electricity to operate and may include a battery for storing charge. In order to provide charge for operation or charge for the battery, a charging accessory may be used for these devices. The charger accessory also provides functionality for authentication, including age verification. Such devices may be restricted based on age or other factors that require some form of authentication, verification, and/or identification to satisfy the restriction. In one example, the accessory may provide or connect with an age verification system for confirming an age of a user. The accessory may be used with any age restricted device. Although applying to any ENDS device, the examples described below may focus on aerosol delivery devices configured to produce aerosol, which may be referred to as electronic cigarettes, heat-not-burn cigarettes (or devices), or no-heat-no-burn devices. The present disclosure includes, without limitation, the following example implementations.

In one implementation, a system includes an age verification system configured to verify an age of a user. The system further includes an aerosol delivery device with a battery provides aerosol to the user. A charging accessory is configured to provide charge to the battery of the aerosol delivery device when the charging accessory is unlocked. The charging accessory is unlocked when the user is authenticated with the age verification system. In one implementation, the user is authenticated by the charging accessory communicating with the age verification system. In one implementation, the charging accessory further includes authentication circuitry configured for the communication with the age verification system. In one implementation, the charging accessory couples a power supply with the aerosol delivery device for charging the battery. In one implementation, the system includes a host device coupled with the charging accessory, and the host device provides the communication with the age verification system over a network. Further, the host device may be the power supply. In one implementation, the system comprises a network through which the age verification system is coupled with the host device.

In one implementation, a charging accessory for an aerosol delivery device includes a power interface that is configured to receive power from a power supply and couple with the aerosol delivery device for providing power to the aerosol delivery device. The charging accessory may include authentication circuitry that is configured to receive an age verification of a user, such that power is not provided to the aerosol delivery device without the age verification.

In one implementation, the authentication circuitry comprises a switch configured to connect a current for the power through the power interface between from the power supply to the aerosol delivery device upon the age verification. The switch does not connect a current for the power through the power interface when the age verification fails.

In one implementation, the age verification comprises an authentication that includes communicating with an age verification system over a network. In one implementation, the authentication is required for each power cycle and references the age verification of the user. In one implementation, the initial age verification operation is performed using identifying documentation such that the authentication that occurs for each power cycle confirms that the user is from the initial age verification operation.

In one implementation, the age verification comprises an initial age verification for a user and comprises subsequent authentications of that user. In one implementation, the initial age verification includes an association of a user with an age, such that the subsequent authentications include requests to authenticate the association with the user. In one implementation, the initial age verification occurs around a time of purchase and the subsequent authentications occur during usage. In one implementation, the charging accessory includes a biometric sensor for the subsequent authentications, and the biometric sensor includes a facial recognition or fingerprint analysis. In one implementation, the facial recognition or the fingerprint analysis for the subsequent authentications compares to data stored from the initial age verification for the user.

In one implementation, the charging accessory comprises a charging cable or charging case.

In one implementation, the power supply comprises a host device. In one implementation, the host device is configured to communicate with an age verification system over a network regarding the age verification. In one implementation, the age verification is communicated from the age verification system to the host device through electric pulses or data pulses.

In one implementation, the aerosol delivery device comprises a battery for heating a liquid to generate an aerosol, and the power is provided from the charger accessory to the aerosol delivery device for charging the battery.

One implementation is a method for operating a charging accessory with an age restricted device. The method includes receiving an age verification for a user. When the age verification is authenticated, a current is connected to the age restricted device. When the age verification is not authenticated, a current is prevented from being provided to the age restricted device when the charging accessory is coupled with the age restricted device. In one implementation, the method includes communicating, over a network, with an age verification system for receiving the age verification of the user. The age verification may include information on whether the user has a verified age or not.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings, which illustrate, by way of example, the principles of some described example implementations.

BRIEF DESCRIPTION OF THE FIGURES

Figure 1:
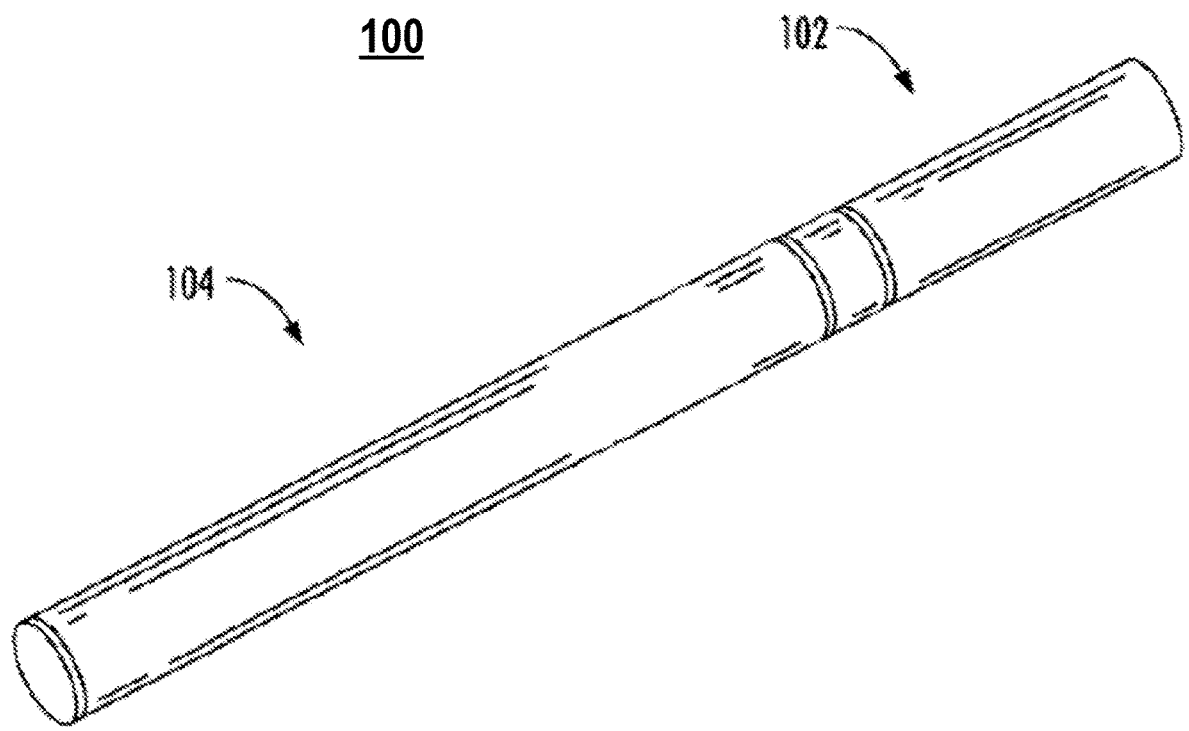
Figure 2:
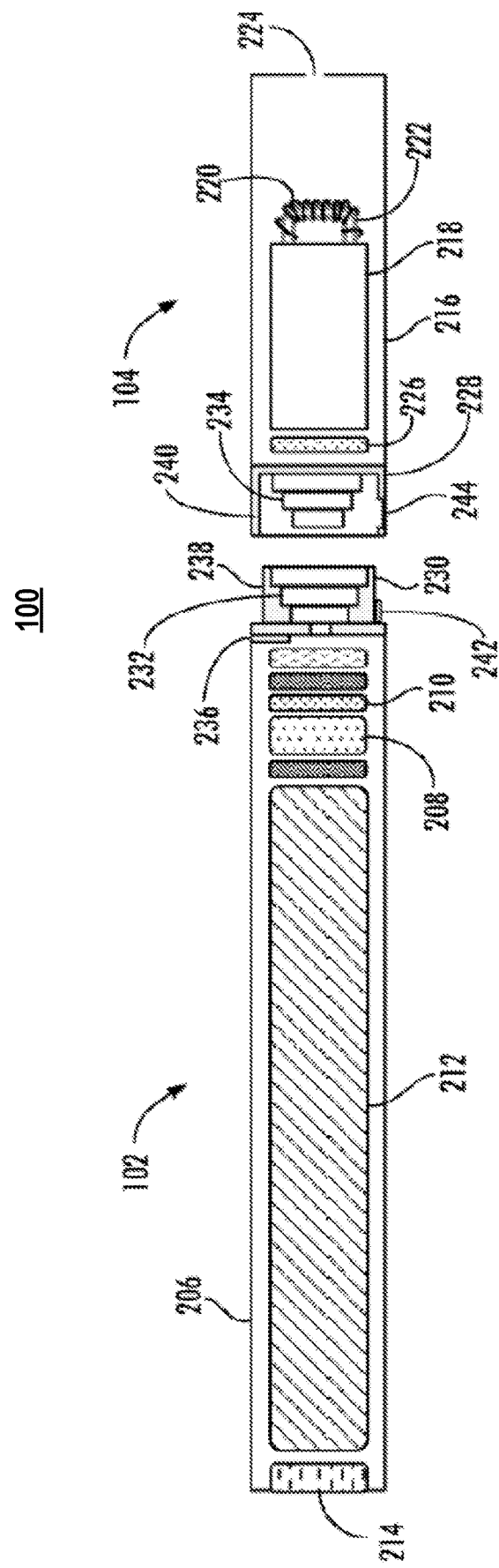
Figure 3:
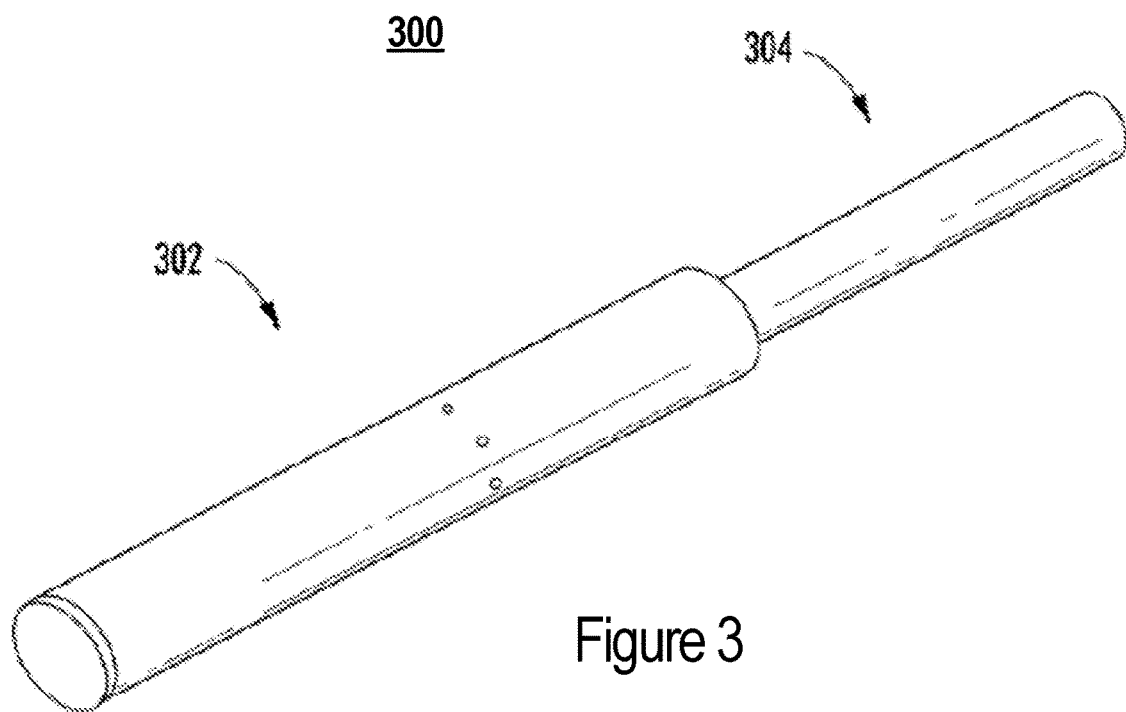
Figure 4:
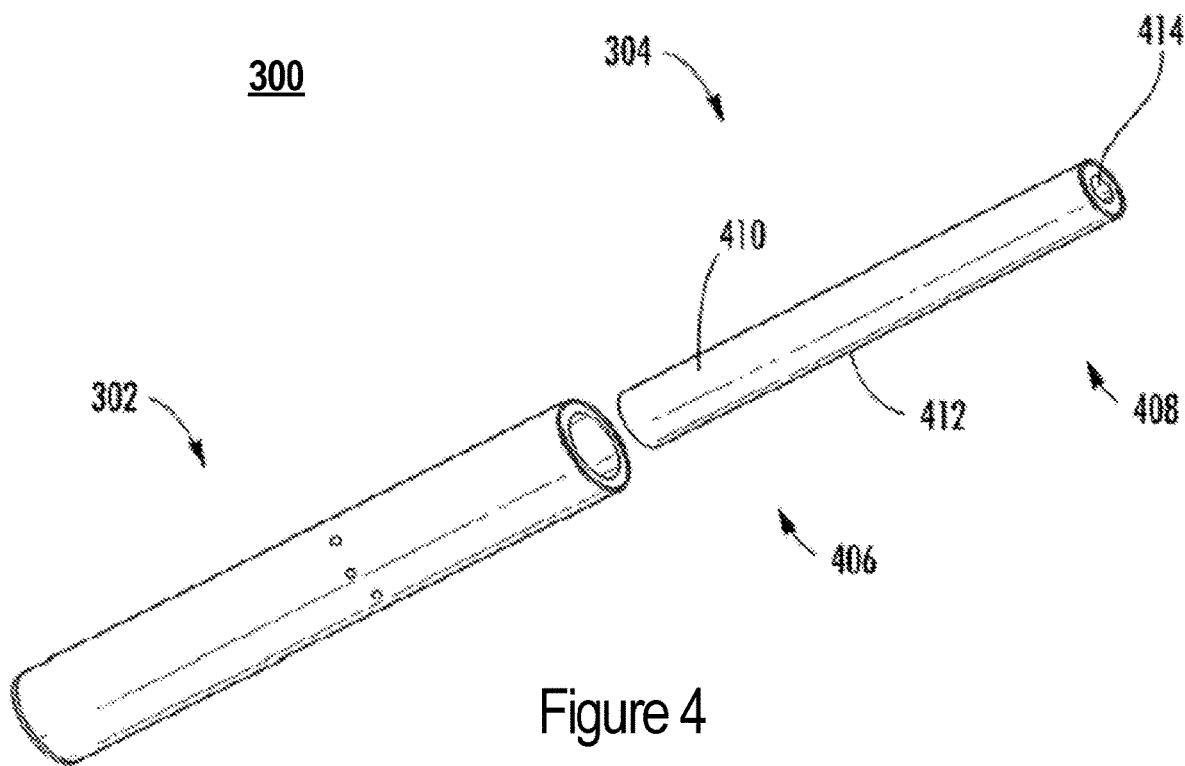
Figure 5:
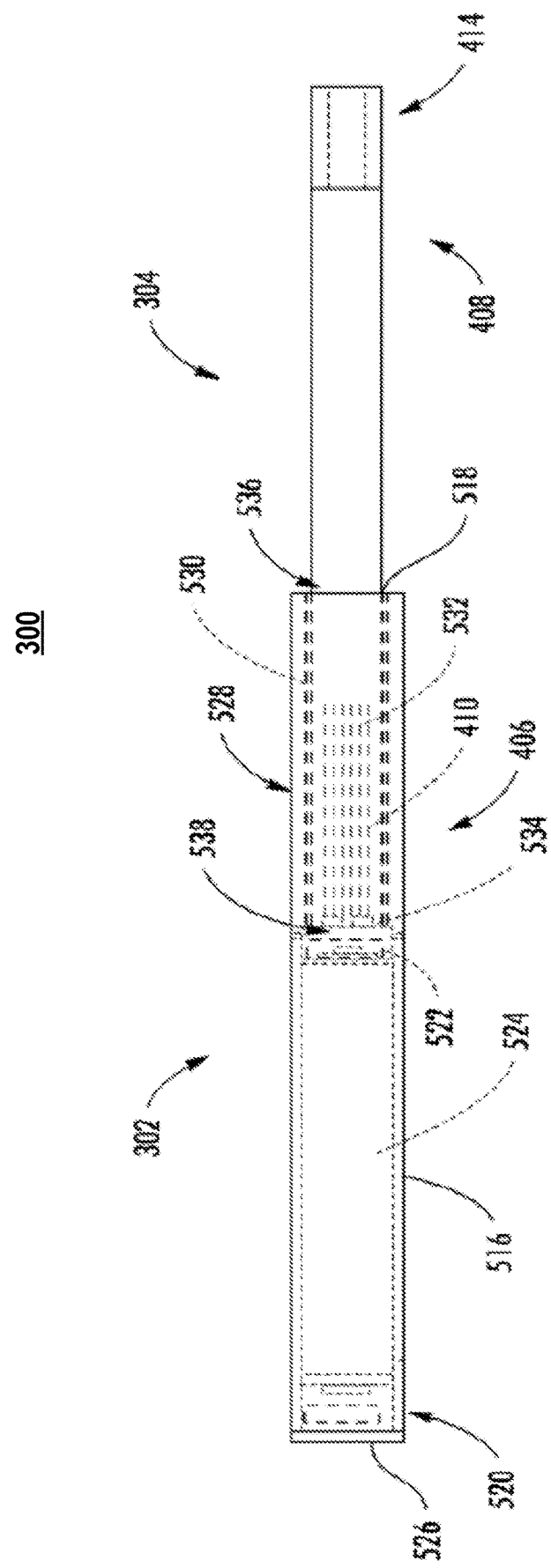
Figure 6:
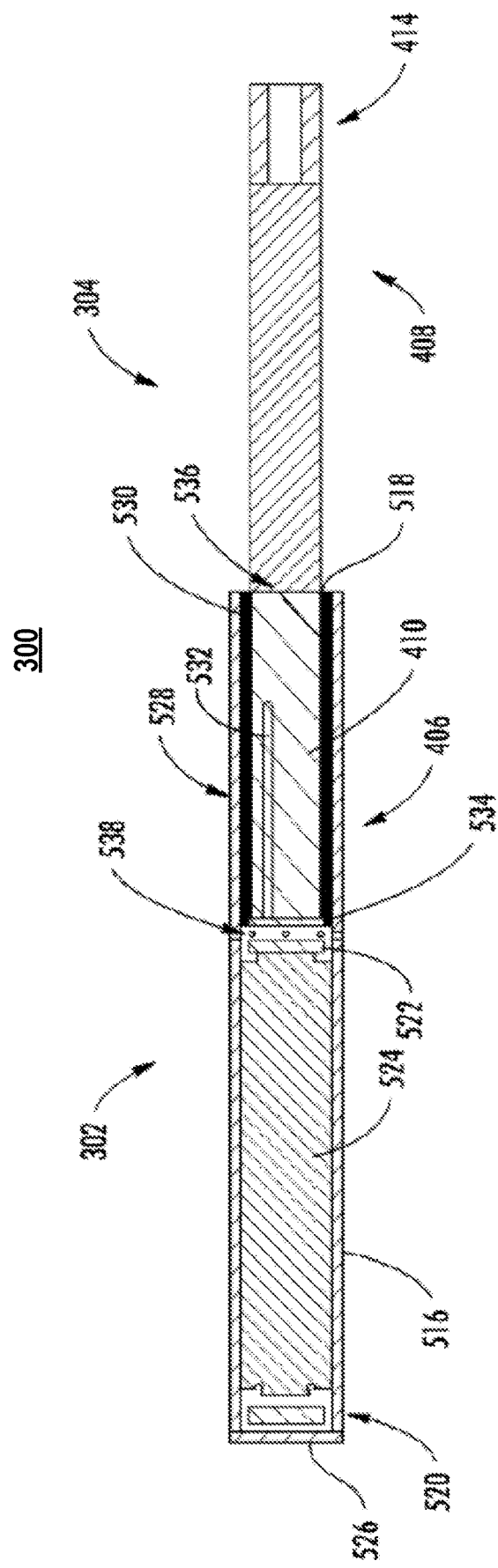
Figure 7:
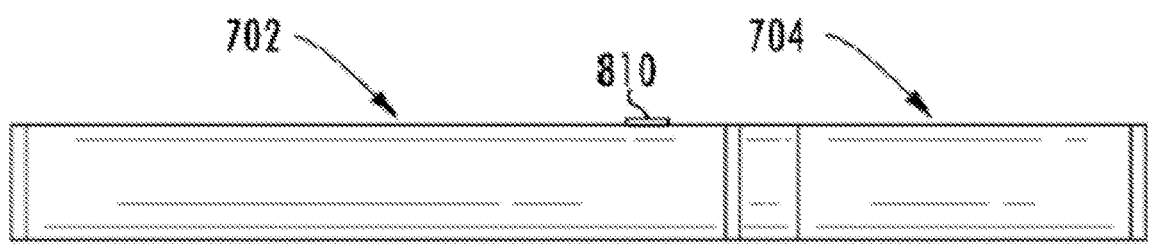
Figure 8:
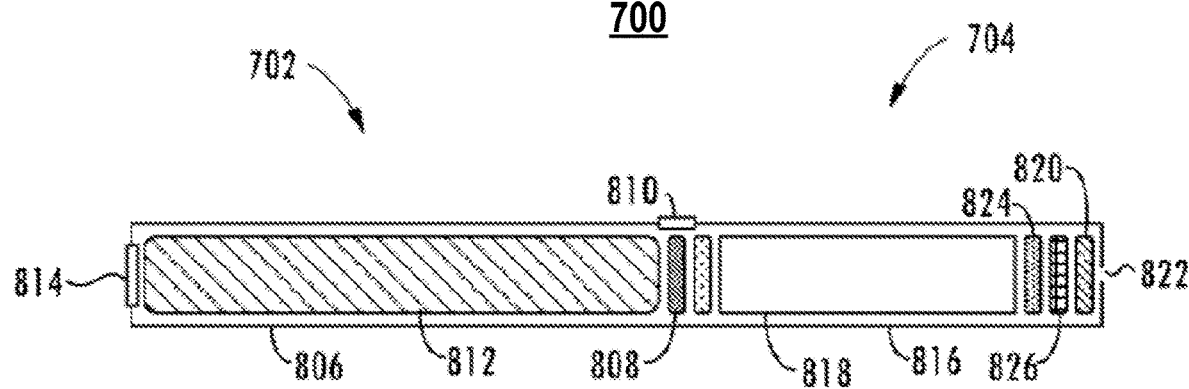
Figure 9:
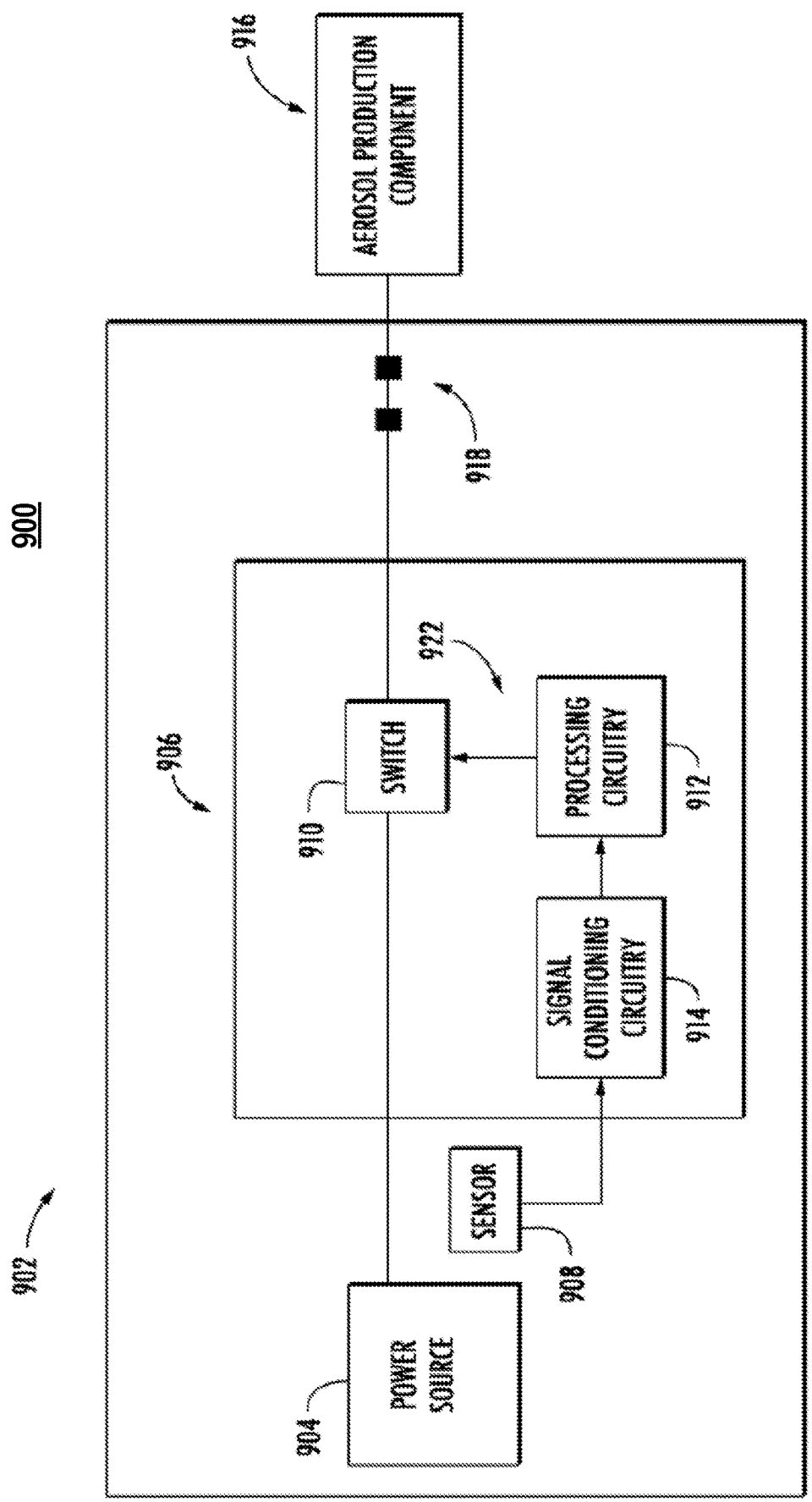
Figure 10:
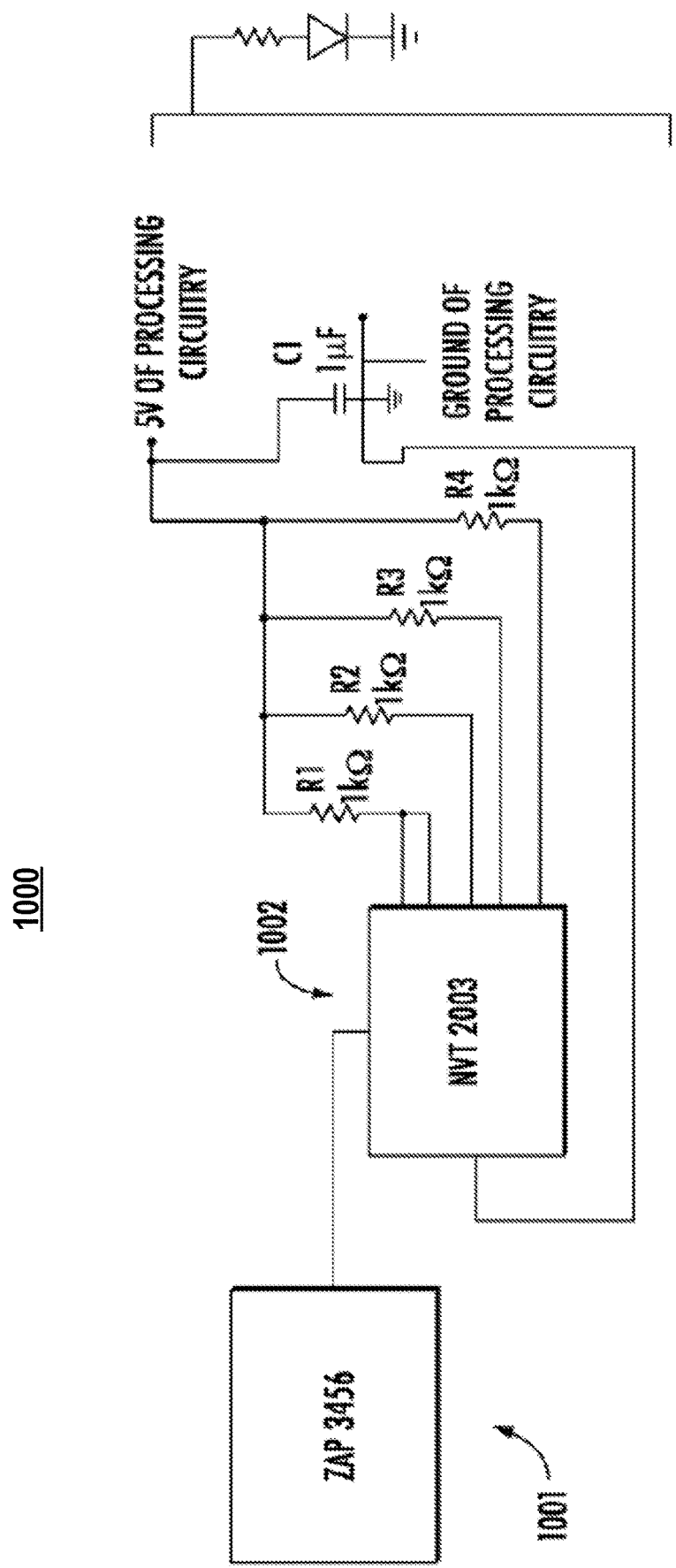

Having thus described aspects of the disclosure in the foregoing general terms, reference will now be made to the accompanying figures, which are not necessarily drawn to scale, and wherein:

FIG. 1 illustrates a perspective view of an aerosol delivery device including a cartridge and a control body that are coupled to one another, according to an example implementation of the present disclosure;

FIG. 2 is a partially cut-away view of the aerosol delivery device of FIG. 1 in which the cartridge and control body are decoupled from one another, according to an example implementation;

FIGS. 3 and 4 illustrate a perspective view of an aerosol delivery device comprising a control body and an aerosol source member that are respectively coupled to one another and decoupled from one another, according to another example implementation of the present disclosure;

FIGS. 5 and 6 illustrate respectively a front view of and a sectional view through the aerosol delivery device of FIGS. 3 and 4, according to an example implementation;

FIGS. 7 and 8 illustrate respectively a side view and a partially cut-away view of an aerosol delivery device including a cartridge coupled to a control body, according to example implementations;

FIG. 9 illustrates a circuit diagram of an aerosol delivery device according to various example implementations of the present disclosure; and FIG. 10 illustrates a circuit diagram of signal conditioning circuitry according to an example implementation of the present disclosure.

Figure 11A:
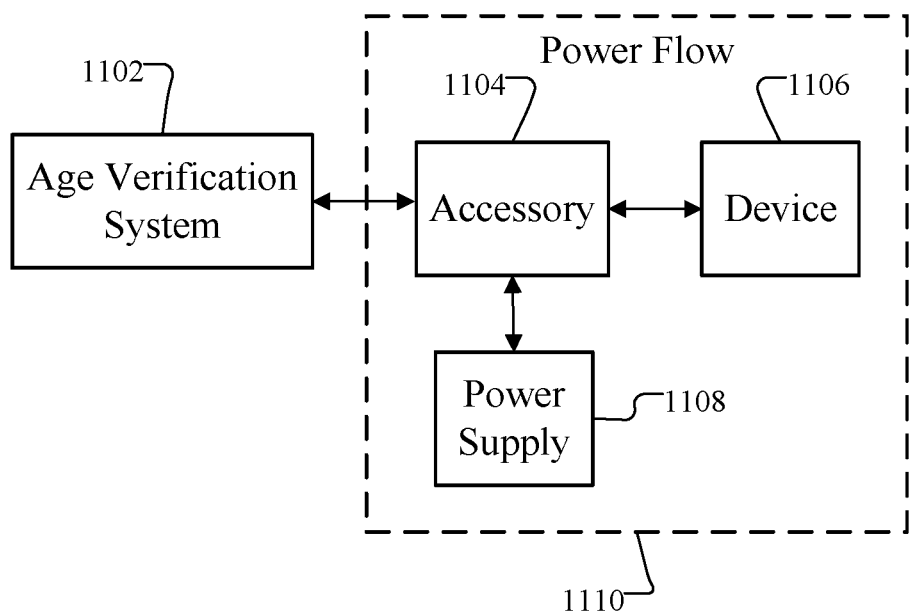
Figure 11B:
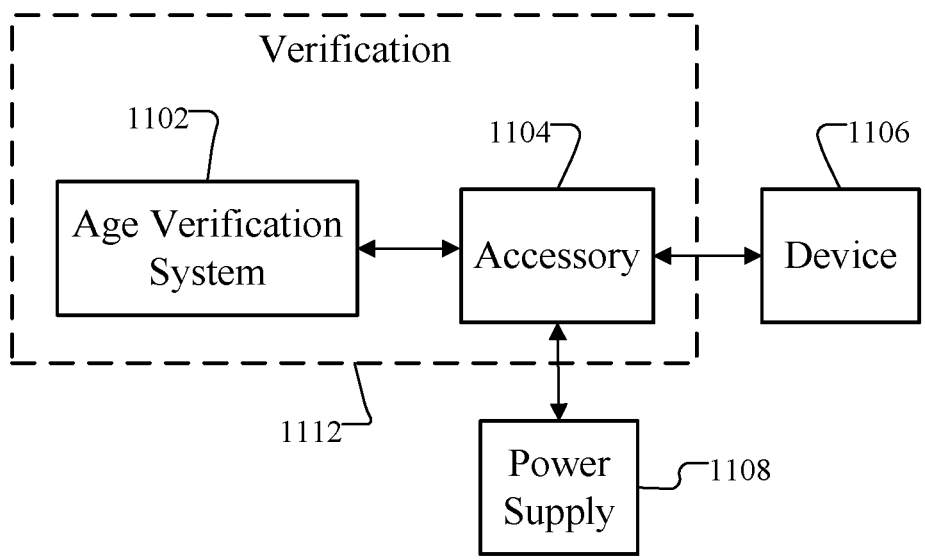

FIG. 11a and FIG. 11b illustrate example system diagrams where FIG. 11a illustrate a power flow portion and FIG. 11b illustrates a verification portion.

Figure 12:
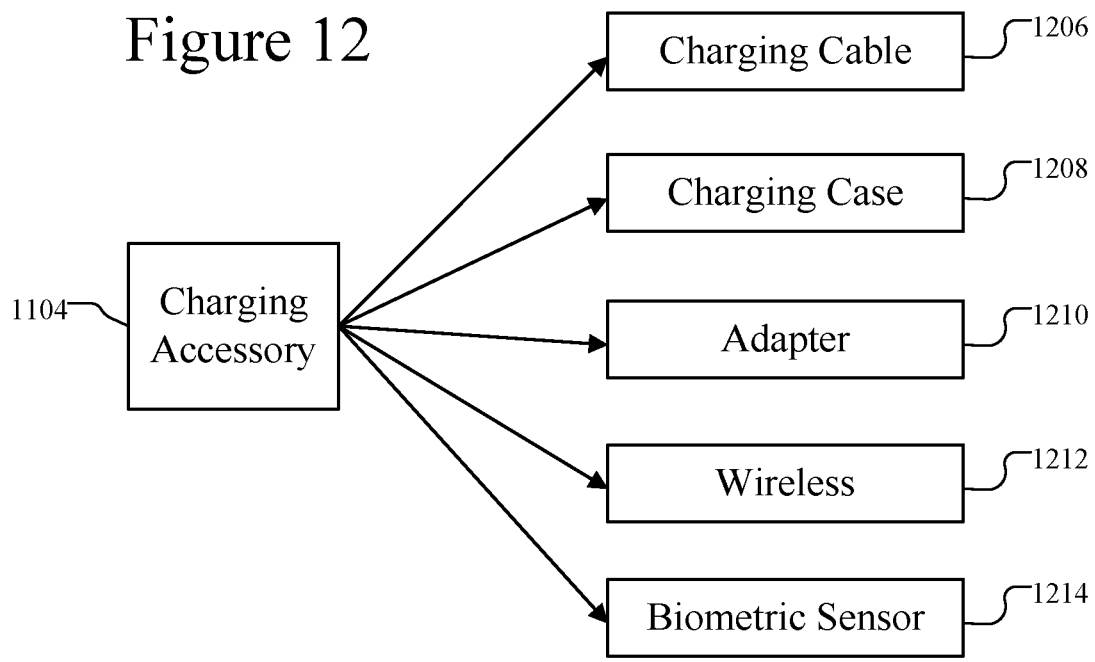

FIG. 12 illustrates example charging accessories.

Figure 13:
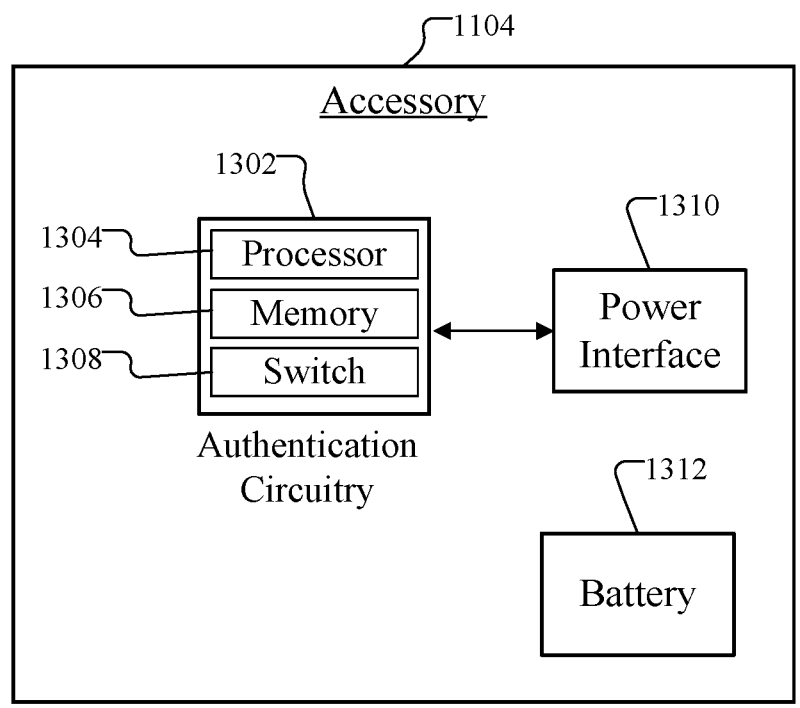

FIG. 13 illustrates an embodiment of the charging accessory.

Figure 14:
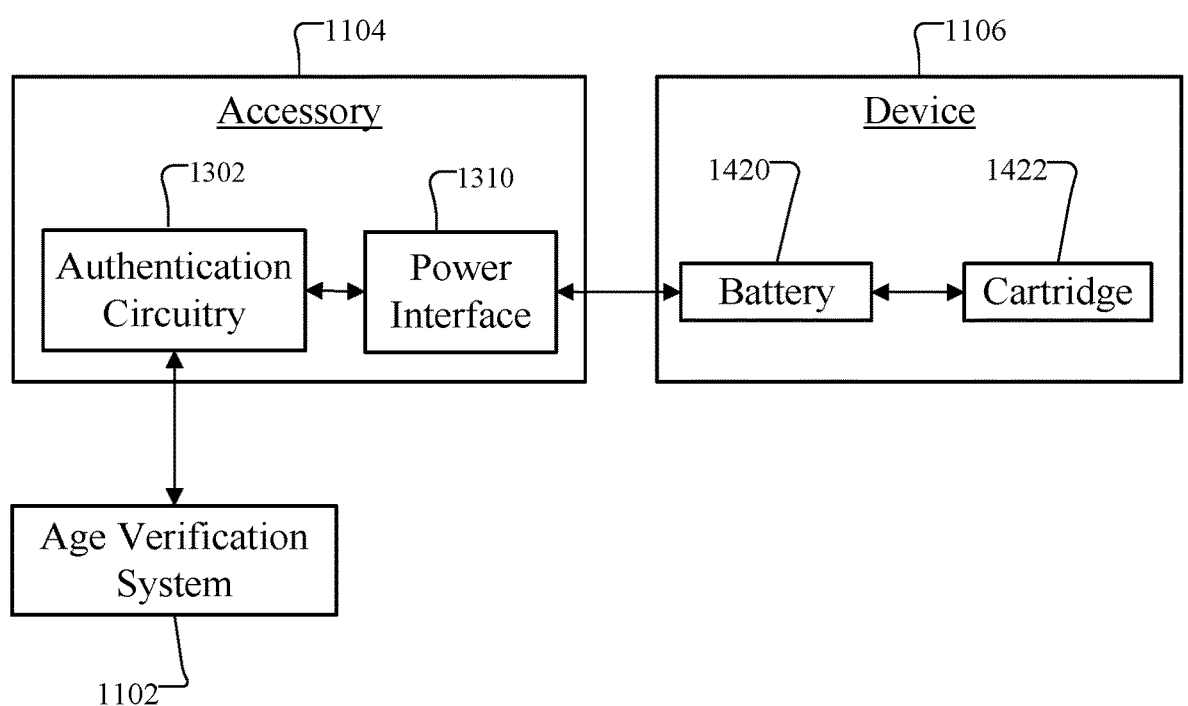

FIG. 14 illustrates an embodiment showing the connection of the charging accessory with the device and the age verification system.

Figure 15:
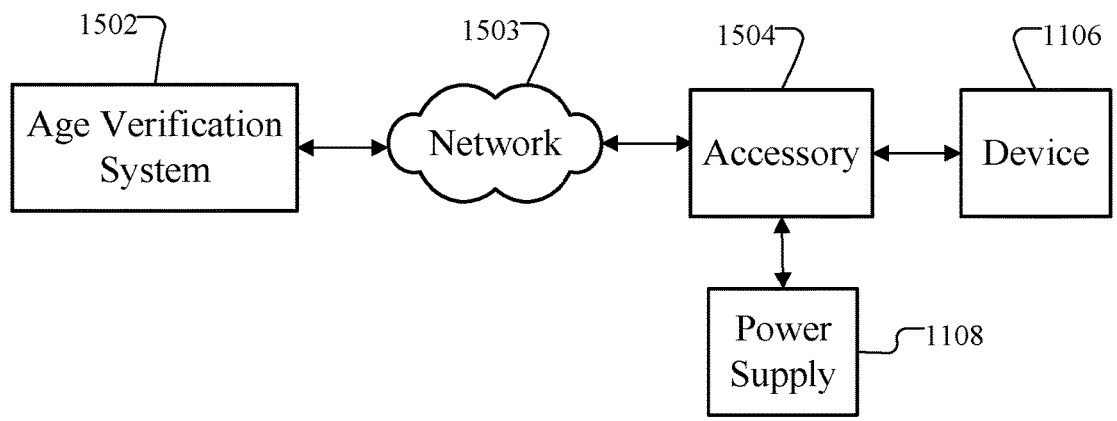

FIG. 15 illustrates an embodiment of the age verification system connected over a network.

Figure 16:
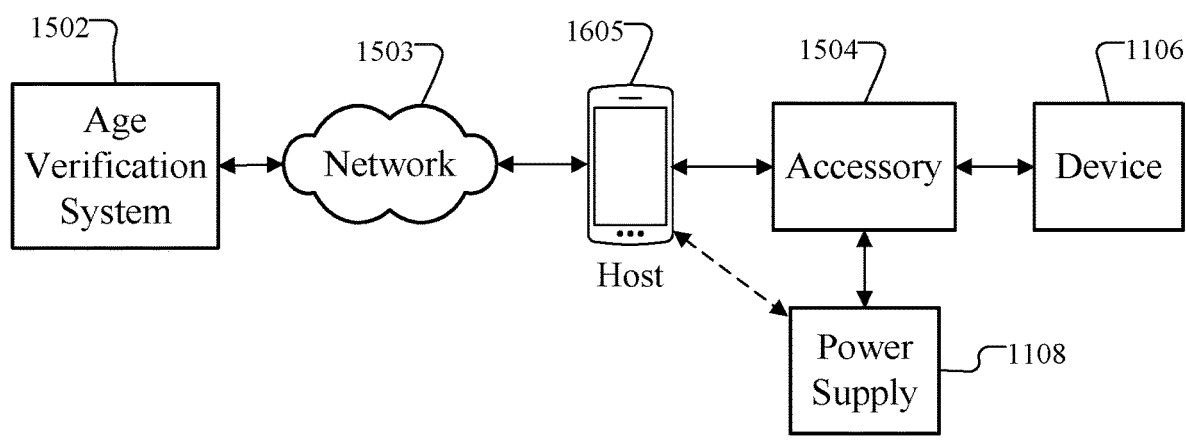

FIG. 16 illustrates an alternative embodiment of the age verification system connected with a host over a network.

Figure 17A:
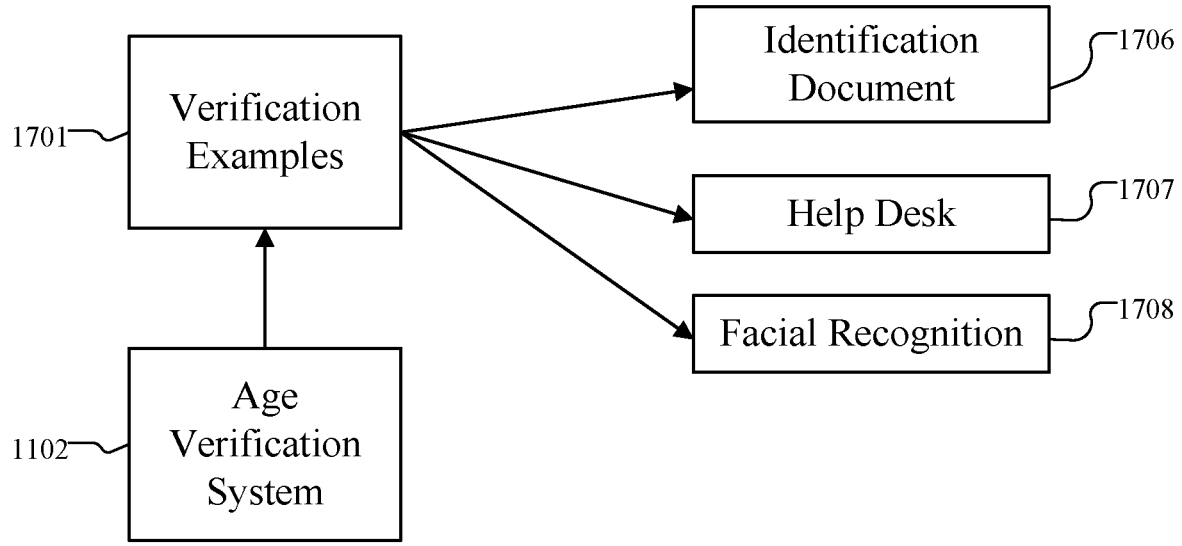

FIG. 17a illustrates verification examples from the age verification system.

Figure 17B:
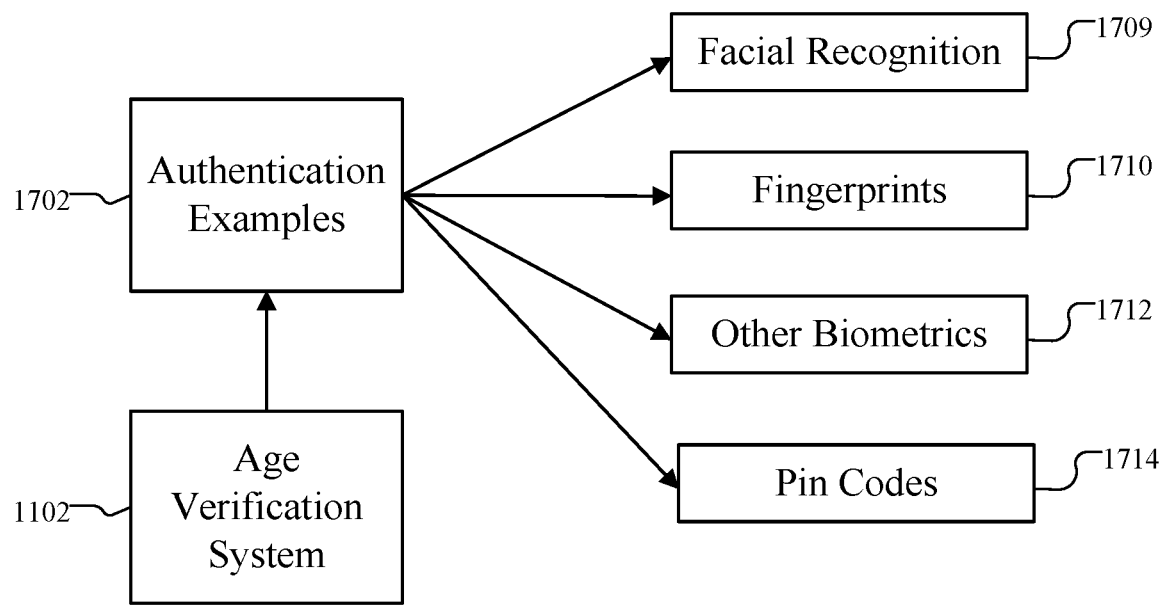

FIG. 17b illustrates authentication examples from the age verification system.

Figure 18:
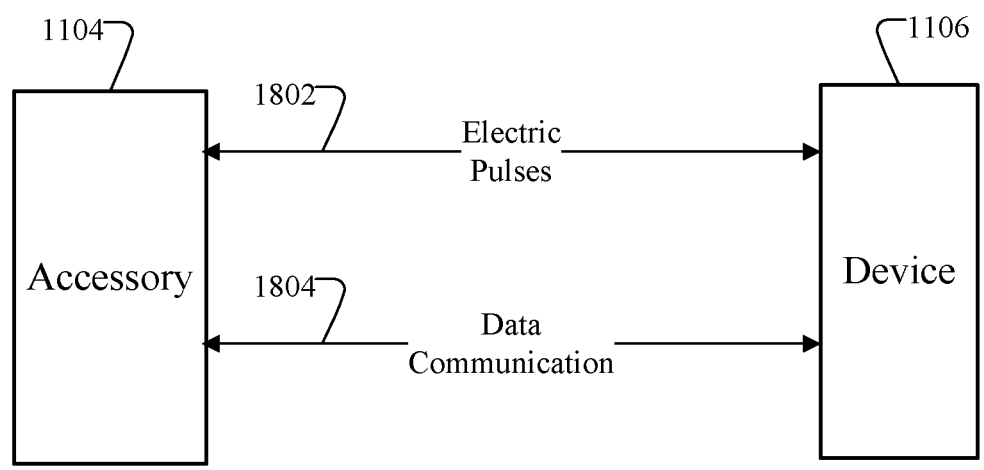

FIG. 18 illustrates example communications between a charger accessory and the device.

Figure 19:
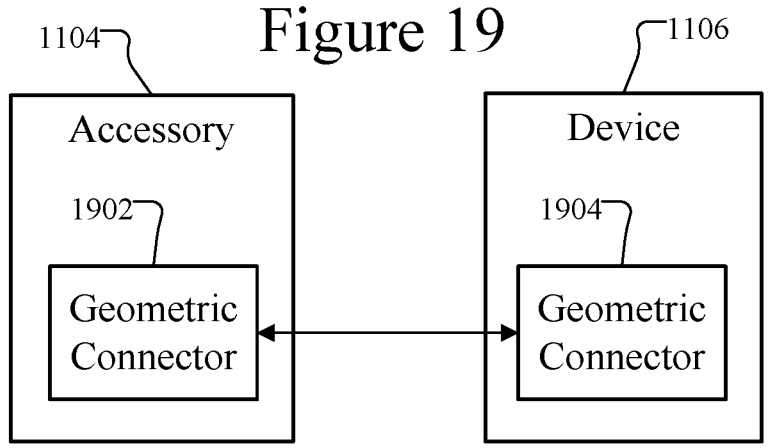

FIG. 19 illustrates a connection between a charger accessory and the device.

Figure 20:
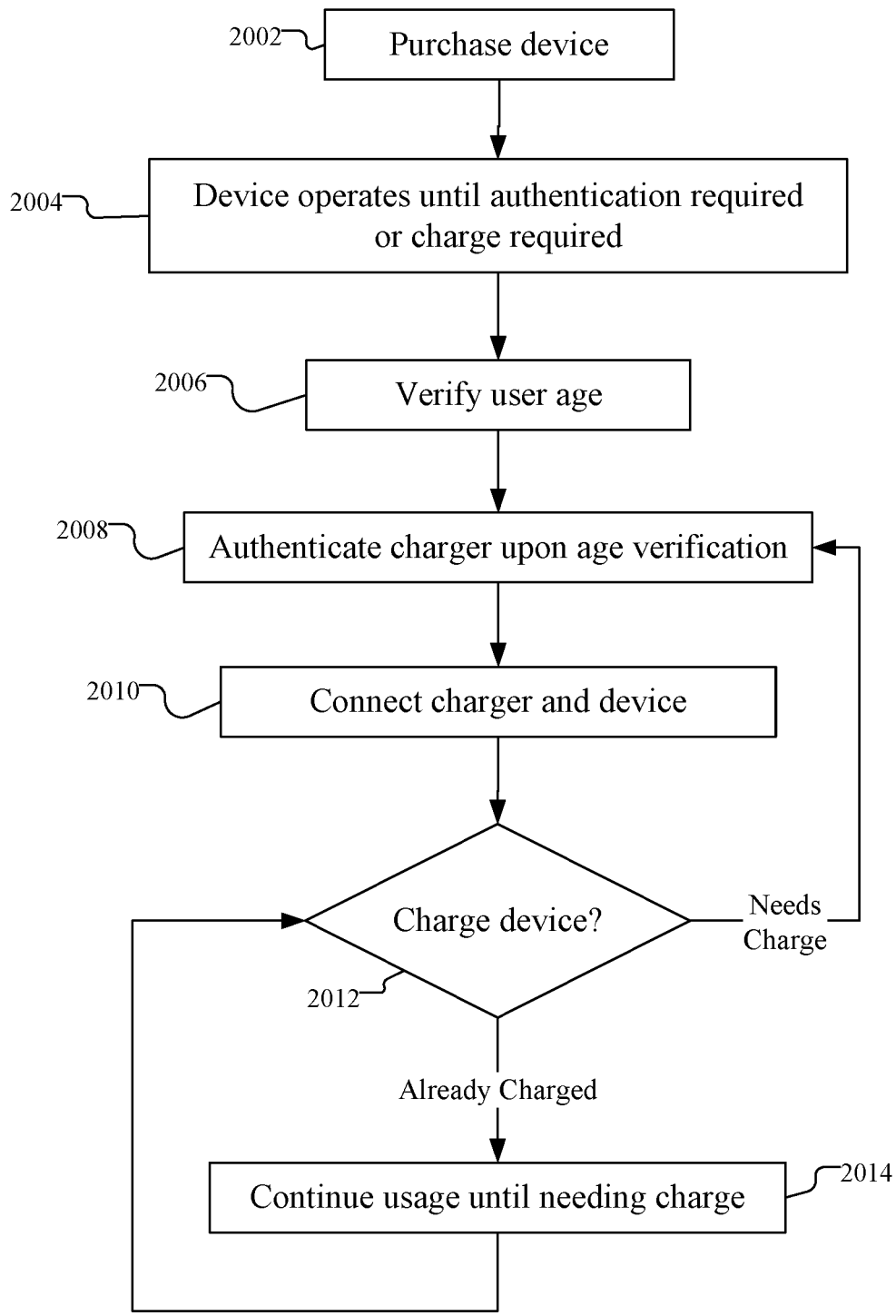

FIG. 20 is a flow chart illustrating the age verification process.

Figure 21:
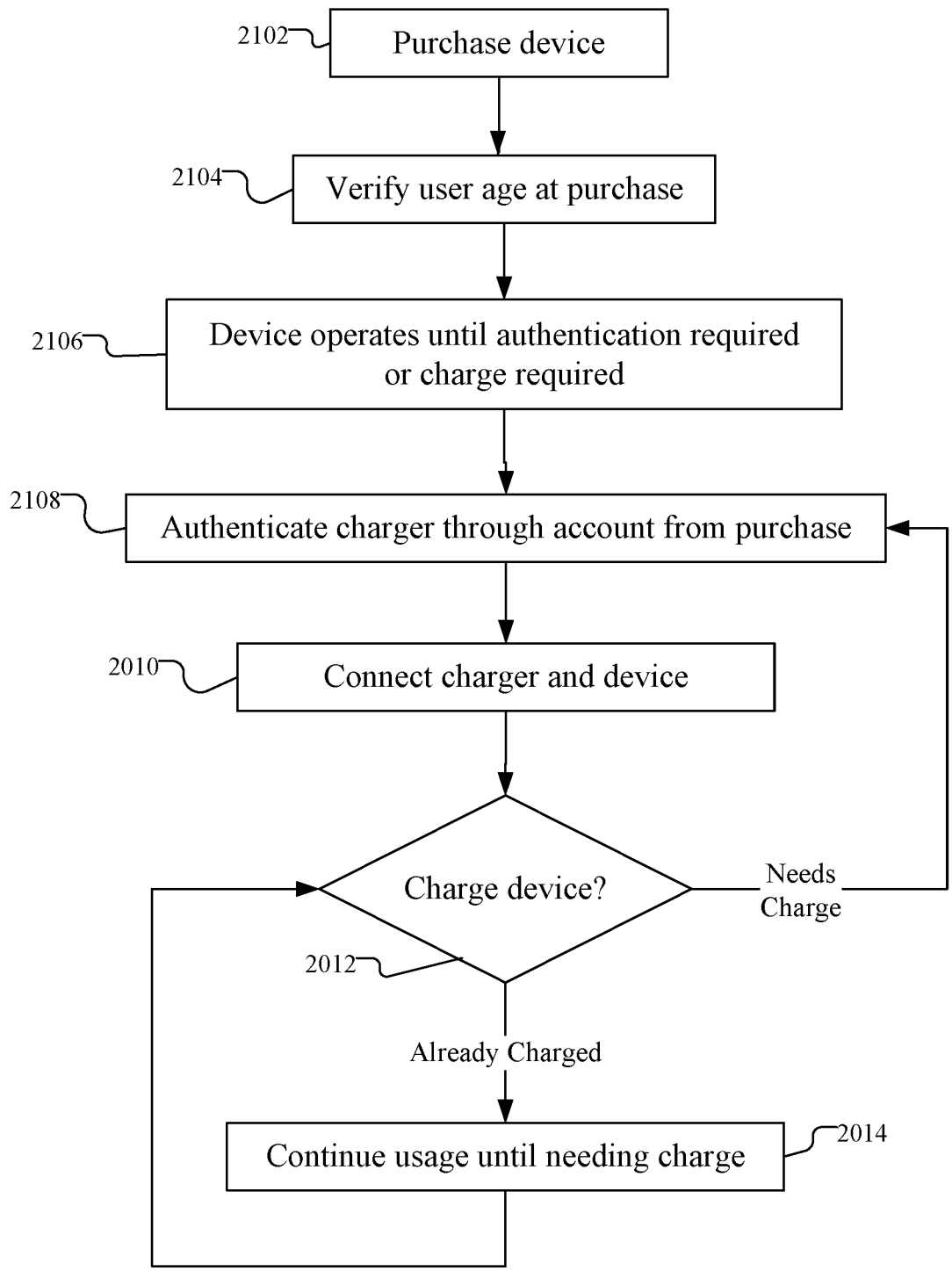

FIG. 21 is a flow chart illustrating an alternative embodiment of the age verification process.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, the present disclosure relates to an accessory, such as a charger, that connects with an electronic nicotine delivery systems ("ENDS") device, which may include aerosol delivery devices. ENDS is one example of such a device that may be associated with restriction, such as an age restriction. Other examples include delivery devices for Tetrahydrocannabinol (THC), Cannabidiol (CBD), botanicals, medicinals, and/or other active ingredients. Thus, it will be appreciated that while an ENDS device, such as an aerosol delivery device, is used as an example application of various embodiments throughout, this example is intended to be non-limiting such that inventive concepts disclosed herein can be used with devices other than ENDS devices, including aerosol delivery devices that may be used to deliver other medicinal and/or active ingredients to a user.

The ENDS or aerosol delivery devices require some form of electricity to operate and may include a battery for storing charge. The charger accessory may provide charge for operation or for charging the battery. In addition, the accessory may provide functionality for authentication, which may be based on age verification, because such devices may be restricted based on age or other factors that require some form of authentication, verification, and/or identification. The accessory may provide or connect with an age verification system for confirming an age of a user. This may be applicable to any age restricted device or substance, including nicotine, cigarettes, alcohol, Tetrahydrocannabinol (THC), Cannabidiol (CBD), CBD oil, cannabis/marijuana, botanicals, medicinals, and/or other age restricted products. FIGS. 1-10 illustrate examples of an age restricted device, but the charging accessory may be applicable to devices other than an aerosol delivery device. Likewise, although age is one example of a restriction that the charger accessory verifies, there may be other types of restrictions on a device that the charger accessory verifies. Example chargers or charging accessories that may be used in combination with various embodiments are further described in U.S. Pat. Pub. No. 2019/0089180 to Rajesh Sur; U.S. Pat. Pub. No. 2015/0224268 to Henry et al.; U.S. Pat. No. 10,206,431 to Sur et al.; each of which is hereby incorporated by reference.

Aerosol delivery devices are one example of a device that may be restricted and require verification from a charger accessory. Aerosol delivery devices are further described with respect to FIGS. 1-10. They may be configured to produce an aerosol (an inhalable substance) from an aerosol precursor composition (sometimes referred to as an inhalable substance medium). The aerosol precursor composition may comprise one or more of a solid tobacco material, a semi-solid tobacco material, or a liquid aerosol precursor composition. In some implementations, the aerosol delivery devices may be configured to heat and produce an aerosol from a fluid aerosol precursor composition (e.g., a liquid aerosol precursor composition). Additionally or alternatively, the aerosol precursor composition may comprise one or more substances mentioned above, including but not limited to botanical substances, medicinal substances, alcohol, glycerin, and may include nicotine, Tetrahydrocannabinol (THC), Cannabidiol (CBD), or other active ingredients. Such aerosol delivery devices may include so-called electronic cigarettes. In other implementations, the aerosol delivery devices may comprise heat-not-burn devices. In yet other implementations, the aerosol delivery devices may comprise no-heat-no-burn devices.

Liquid aerosol precursor composition, also referred to as a vapor precursor composition or "e-liquid," is particularly useful for electronic cigarettes and no-heat-no-burn devices. Liquid aerosol precursor composition may comprise a variety of components including, by way of example, a polyhydric alcohol (e.g., glycerin, propylene glycol, or a mixture thereof), nicotine, tobacco, tobacco extract, and/or flavorants. In some examples, the aerosol precursor composition comprises glycerin and nicotine. In other examples, the composition may additionally or alternatively include alcohol, other botanical substances, other medicinal substances, or may include Tetrahydrocannabinol (THC), Cannabidiol (CBD), or other active ingredients, or some combination thereof.

Some liquid aerosol precursor compositions that may be used in conjunction with various implementations may include one or more acids such as levulinic acid, succinic acid, lactic acid, pyruvic acid, benzoic acid, fumaric acid, combinations thereof, and the like. Inclusion of an acid(s) in liquid aerosol precursor compositions including nicotine may provide a protonated liquid aerosol precursor composition, including nicotine in salt form. Representative types of liquid aerosol precursor components and formulations are set forth and characterized in U.S. Pat. No. 7,726,320 to Robinson et al.; U.S. Pat. No. 9,254,002 to Chong et al.; and U.S. Pat. App. Pub. Nos. 2013/0008457 to Zheng et al., 2015/0020823 to Lipowicz et al., and 2015/0020830 to Koller; as well as PCT Pat. App. Pub. No. WO 2014/182736 to Bowen et al.; and U.S. Pat. No. 8,881,737 to Collett et al., the disclosures of which are incorporated herein by reference. Other aerosol precursors that may be employed include the aerosol precursors that have been incorporated in any of a number of the representative products identified above. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN. Implementations of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al.; U.S. Pat. No. 8,627,828 to Strickland et al.; and U.S. Pat. No. 9,307,787 to Sun et al.; as well as U.S. Pat. App. Pub. Nos. 2010/0018539 to Brinkley et al., and PCT Pat. App. Pub. No. WO 97/06786 to Johnson et al., all of which are incorporated by reference herein.

Representative types of substrates, reservoirs or other components for supporting the aerosol precursor are described in U.S. Pat. No. 8,528,569 to Newton; U.S. Pat. App. Pub. No. 2014/0261487 to Chapman et al.; U.S. Pat. App. Pub. No. 2015/0059780 to Davis et al.; and U.S. Pat. App. Pub. No. 2015/0216232 to Bless et al., all of which are incorporated herein by reference. Additionally, various wicking materials, and the configuration and operation of those wicking materials within certain types of electronic cigarettes, are set forth in U.S. Pat. No. 8,910,640 to Sears et al., which is incorporated herein by reference.

In other implementations, the aerosol delivery devices may comprise heat-not-burn devices, configured to heat a solid aerosol precursor composition (e.g., an extruded tobacco rod) or a semi-solid aerosol precursor composition (e.g., a glycerin-loaded tobacco paste). The aerosol precursor composition may comprise tobacco-containing beads, tobacco shreds, tobacco strips, reconstituted tobacco material, or combinations thereof, and/or a mix of finely ground tobacco, tobacco extract, spray dried tobacco extract, or other tobacco form mixed with optional inorganic materials (such as calcium carbonate), optional flavors, and aerosol forming materials to form a substantially solid or moldable (e.g., extrudable) substrate. Representative types of solid and semi-solid aerosol precursor compositions and formulations are disclosed in U.S. Pat. No. 8,424,538 to Thomas et al.; U.S. Pat. No. 8,464,726 to Sebastian et al.; U.S. Pat. App. Pub. No. 2015/0083150 to Conner et al.; U.S. Pat. App. Pub. No. 2015/0157052 to Ademe et al.; and U.S. Pat. App. Pub. No. 2017/0000188 to Nordskog et al., all of which are incorporated by reference herein. Further representative types of solid and semi-solid aerosol precursor compositions and arrangements include those found in the NEOSTIKS™ consumable aerosol source members for the GLO™ product by British American Tobacco and in the HEETS™ consumable aerosol source members for the IQOS™ product by Philip Morris International, Inc.

In various implementations, the inhalable substance specifically may be a tobacco component or a tobacco-derived material (i.e., a material that is found naturally in tobacco that may be isolated directly from the tobacco or synthetically prepared). For example, the aerosol precursor composition may comprise tobacco extracts or fractions thereof combined with an inert substrate. The aerosol precursor composition may further comprise unburned tobacco or a composition containing unburned tobacco that, when heated to a temperature below its combustion temperature, releases an inhalable substance. In some implementations, the aerosol precursor composition may comprise tobacco condensates or fractions thereof (i.e., condensed components of the smoke produced by the combustion of tobacco, leaving flavors and, possibly, nicotine).

Tobacco materials useful in the present disclosure can vary and may include, for example, flue-cured tobacco, burley tobacco, Oriental tobacco or Maryland tobacco, dark tobacco, dark-fired tobacco and Rustica tobaccos, as well as other rare or specialty tobaccos, or blends thereof. Tobacco materials also can include so-called "blended" forms and processed forms, such as processed tobacco stems (e.g., cut-rolled or cut-puffed stems), volume expanded tobacco (e.g., puffed tobacco, such as dry ice expanded tobacco (DIET), preferably in cut filler form), reconstituted tobaccos (e.g., reconstituted tobaccos manufactured using paper-making type or cast sheet type processes). Various representative tobacco types, processed types of tobaccos, and types of tobacco blends are set forth in U.S. Pat. No. 4,836,224 to Lawson et al., U.S. Pat. No. 4,924,888 to Perfetti et al., U.S. Pat. No. 5,056,537 to Brown et al., U.S. Pat. No. 5,159,942 to Brinkley et al., U.S. Pat. No. 5,220,930 to Gentry, U.S. Pat. No. 5,360,023 to Blakley et al., U.S. Pat. No. 6,701,936 to Shafer et al., U.S. Pat. No. 7,011,096 to Li et al., U.S. Pat. No. 7,017,585 to Li et al., and U.S. Pat. No. 7,025,066 to Lawson et al.; U.S. Pat. App. Pub. No. 2004/0255965 to Perfetti et al.; PCT Pat. App. Pub. No. WO 02/37990 to Bereman; and Bombick et al., Fund. Appl. Toxicol., 39, p. 11-17 (1997), which are incorporated herein by reference. Further example tobacco compositions that may be useful in a smoking device, including according to the present disclosure, are disclosed in U.S. Pat. No. 7,726,320 to Robinson et al., which is incorporated herein by reference.

Still further, the aerosol precursor composition may comprise an inert substrate having the inhalable substance, or a precursor thereof, integrated therein or otherwise deposited thereon. For example, a liquid comprising the inhalable substance may be coated on or absorbed or adsorbed into the inert substrate such that, upon application of heat, the inhalable substance is released in a form that can be withdrawn from the inventive article through application of positive or negative pressure. In some aspects, the aerosol precursor composition may comprise a blend of flavorful and aromatic tobaccos in cut filler form. In another aspect, the aerosol precursor composition may comprise a reconstituted tobacco material, such as described in U.S. Pat. No. 4,807,809 to Pryor et al.; U.S. Pat. No. 4,889,143 to Pryor et al.; and U.S. Pat. No. 5,025,814 to Raker, the disclosures of which are incorporated herein by reference. For further information regarding suitable aerosol precursor composition, see U.S. patent application Ser. No. 15/916,834 to Sur et al., filed Mar. 9, 2018, which is incorporated herein by reference.

Regardless of the type of aerosol precursor composition, aerosol delivery devices may include an aerosol production component configured to produce an aerosol from the aerosol precursor composition. In the case of an electronic cigarette or a heat-not-burn device, for example, the aerosol production component may be or include a heating element. In the case of a no-heat-no-burn device, in some examples, the aerosol production component may be or include a vibratable piezoelectric or piezomagnetic mesh.

One example of a suitable heating element is an induction heater. Such heaters often comprise an induction transmitter and an induction receiver. The induction transmitter may include a coil configured to create an oscillating magnetic field (e.g., a magnetic field that varies periodically with time) when alternating current is directed through it. The induction receiver may be at least partially located or received within the induction transmitter and may include a conductive material (e.g., ferromagnetic material or an aluminum coated material). By directing alternating current through the induction transmitter, eddy currents may be generated in the induction receiver via induction. The eddy currents flowing through the resistance of the material defining the induction receiver may heat it by Joule heating (i.e., through the Joule effect). The induction receiver, which may define an atomizer, may be wirelessly heated to form an aerosol from an aerosol precursor composition positioned in proximity to the induction receiver. Various implementations of an aerosol delivery device with an induction heater are described in U.S. Pat. App. Pub. No. 2017/0127722 to Davis et al.; U.S. Pat. App. Pub. No. 2017/0202266 to Sur et al.; U.S. patent application Ser. No. 15/352,153 to Sur et al., filed Nov. 15, 2016; U.S. Pat. App. Ser. No. 15/799,365 to Sebastian et al., filed Oct. 31, 2017; and U.S. patent application Ser. No. 15/836,086 to Sur, all of which are incorporated by reference herein.

In other implementations including those described more particularly herein, the heating element is a conductive heater such as in the case of electrical resistance heater. These heaters may be configured to produce heat when an electrical current is directed through it. In various implementations, a conductive heater may be provided in a variety forms, such as in the form of a foil, a foam, discs, spirals, fibers, wires, films, yarns, strips, ribbons or cylinders. Such heaters often include a metal material and are configured to produce heat as a result of the electrical resistance associated with passing an electrical current through it. Such resistive heaters may be positioned in proximity to and heat an aerosol precursor composition to produce an aerosol. A variety of conductive substrates that may be usable with the present disclosure are described in the above-cited U.S. Pat. App. Pub. No. 2013/0255702 to Griffith et al.

In some implementations aerosol delivery devices may include a control body and a cartridge in the case of so-called electronic cigarettes or no-heat-no-burn devices, or a control body and an aerosol source member in the case of heat-not-burn devices. In the case of either electronic cigarettes or heat-not-burn devices, the control body may be reusable, whereas the cartridge/aerosol source member may be configured for a limited number of uses and/or configured to be disposable. Various mechanisms may connect the cartridge/aerosol source member to the control body to result in a threaded engagement, a press-fit engagement, an interference fit, a sliding fit, a magnetic engagement, or the like.

The control body and cartridge/aerosol source member may include separate, respective housings or outer bodies, which may be formed of any of a number of different materials. The housing may be formed of any suitable, structurally-sound material. In some examples, the housing may be formed of a metal or alloy, such as stainless steel, aluminum or the like. Other suitable materials include various plastics (e.g., polycarbonate), metal-plating over plastic, ceramics and the like.

The cartridge/aerosol source member may include the aerosol precursor composition. In order to produce aerosol from the aerosol precursor composition, the aerosol production component (e.g., heating element, piezoelectric/piezomagnetic mesh) may be positioned in contact with or proximate the aerosol precursor composition, such as across the control body and cartridge, or in the control body in which the aerosol source member may be positioned. The control body may include a power source, which may be rechargeable or replaceable, and thereby the control body may be reused with multiple cartridges/aerosol source members. The recharging may be with a charging accessory as further described with respect to FIGS. 11-21.

The control body may also include means to activate the aerosol delivery device such as a pushbutton, touch-sensitive surface or the like for manual control of the device. Additionally or alternatively, the control body may include a flow sensor to detect when a user draws on the cartridge/aerosol source member to thereby activate the aerosol delivery device.

In various implementations, the aerosol delivery device according to the present disclosure may have a variety of overall shapes, including, but not limited to an overall shape that may be defined as being substantially rod-like or substantially tubular shaped or substantially cylindrically shaped. In the implementations shown in and described with reference to the accompanying figures, the aerosol delivery device has a substantially round cross-section; however, other cross-sectional shapes (e.g., oval, square, rectangle, triangle, etc.) also are encompassed by the present disclosure. Such language that is descriptive of the physical shape of the article may also be applied to the individual components thereof, including the control body and the cartridge/aerosol source member. In other implementations, the control body may take another handheld shape, such as a small box shape.

In more specific implementations, one or both of the control body and the cartridge/aerosol source member may be referred to as being disposable or as being reusable. For example, the control body may have a power source such as a replaceable battery or a rechargeable battery, SSB, thin-film SSB, rechargeable supercapacitor, lithium-ion or hybrid lithium-ion supercapacitor, or the like. One example of a power source is a TKI-1550 rechargeable lithium-ion battery produced by Tadiran Batteries GmbH of Germany. In another implementation, a useful power source may be a N50-AAA CADNICA nickel-cadmium cell produced by Sanyo Electric Company, Ltd., of Japan. In other implementations, a plurality of such batteries, for example providing 1.2-volts each, may be connected in series. In some implementations, the power source is configured to provide an output voltage. The power source can power the aerosol production component that is powerable to produce an aerosol from an aerosol precursor composition. The power source may be connected with any type of recharging technology, such as a charging accessory as further discussed below.

Examples of power sources are described in U.S. Pat. No. 9,484,155 to Peckerar et al.; and U.S. Pat. App. Pub. No. 2017/0112191 to Sur et al., filed Oct. 21, 2015, the disclosures of which are incorporated herein by reference. Other examples of a suitable power source are provided in U.S. Pat. App. Pub. No. 2014/0283855 to Hawes et al., U.S. Pat. App. Pub. No. 2014/0014125 to Fernando et al., U.S. Pat. App. Pub. No. 2013/0243410 to Nichols et al., U.S. Pat. App. Pub. No. 2010/0313901 to Fernando et al., and U.S. Pat. No. 9,439,454 to Fernando et al., all of which are incorporated herein by reference. With respect to the flow sensor, representative current regulating components and other current controlling components including various microcontrollers, sensors, and switches for aerosol delivery devices are described in U.S. Pat. No. 4,735,217 to Gerth et al.; U.S. Pat. Nos. 4,922,901, 4,947,874, and 4,947,875, all to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al.; U.S. Pat. No. 8,205,622 to Pan; U.S. Pat. No. 8,881,737 to Collet et al.; U.S. Pat. No. 9,423,152 to Ampolini et al.; U.S. Pat. No. 9,439,454 to Fernando et al.; and U.S. Pat. App. Pub. No. 2015/0257445 to Henry et al., all of which are incorporated herein by reference.

Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat.

No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference. Further, U.S. Pat. App. Pub. No. 2017/0099877 to Worm et al., discloses capsules that may be included in aerosol delivery devices and fob-shape configurations for aerosol delivery devices, and is incorporated herein by reference. A variety of the materials disclosed by the foregoing documents may be incorporated into the present devices in various implementations, and all of the foregoing disclosures are incorporated herein by reference.

Yet other features, controls or components that can be incorporated into aerosol delivery devices of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. No. 2005/0016550 to Katase; U.S. Pat. No. 8,689,804 to Fernando et al.; U.S. Pat. App. Pub. No. 2013/0192623 to Tucker et al.; U.S. Pat. No. 9,427,022 to Leven et al.; U.S. Pat. App. Pub. No. 2013/0180553 to Kim et al.; U.S. Pat. App. Pub. No. 2014/0000638 to Sebastian et al.; U.S. Pat. App. Pub. No. 2014/0261495 to Novak et al.; and U.S. Pat. No. 9,220,302 to DePiano et al., all of which are incorporated herein by reference.

In another aspect, the present disclosure may be directed to kits that provide a variety of components as described herein. For example, a kit may comprise a control body with one or more cartridges or aerosol source members. A kit may further include the charging accessory described below, along with one or more batteries, and a control body with one or more cartridges. A kit may further include the charging accessory described below, and a control body with one or more cartridges. A kit may further include the charging accessory described below, along with one or more batteries. In further embodiments, a kit may comprise a plurality of cartridges. A kit may further comprise a plurality of cartridges and one or more batteries and/or the charging accessory described below. In the above embodiments, the cartridges or the control bodies may be provided with a heating member inclusive thereto. The inventive kits may further include a case (or other packaging, carrying, or storage component) that accommodates one or more of the further kit components. Alternatively, the charging accessory may be a case in one of the kits. The case could be a reusable hard or soft container. Further, the case could be simply a box or other packaging structure.

FIGS. 1 and 2 illustrate implementations of an aerosol delivery device including a control body and a cartridge in the case of an electronic cigarette. In this regard, FIGS. 1 and 2 illustrate an aerosol delivery device 100 according to an example implementation of the present disclosure. As indicated, the aerosol delivery device may include a control body 102 and a cartridge 104. The control body and the cartridge can be permanently or detachably aligned in a functioning relationship. In this regard, FIG. 1 illustrates a perspective view of the aerosol delivery device in a coupled configuration, whereas FIG. 2 illustrates a partially cut-away side view of the aerosol delivery device in a decoupled configuration. The aerosol delivery device may, for example, be substantially rod-like, substantially tubular shaped, or substantially cylindrically shaped in some implementations when the control body and the cartridge are in an assembled configuration.

The control body 102 and the cartridge 104 can be configured to engage one another by a variety of connections, such as a press fit (or interference fit) connection, a threaded connection, a magnetic connection, or the like. As such, the control body may include a first engaging element (e.g., a coupler) that is adapted to engage a second engaging element (e.g., a connector) on the cartridge. The first engaging element and the second engaging element may be reversible. As an example, either of the first engaging element or the second engaging element may be a male thread, and the other may be a female thread. As a further example, either the first engaging element or the second engaging element may be a magnet, and the other may be a metal or a matching magnet. In particular implementations, engaging elements may be defined directly by existing components of the control body and the cartridge. For example, the housing of the control body may define a cavity at an end thereof that is configured to receive at least a portion of the cartridge (e.g., a storage tank or other shell-forming element of the cartridge). In particular, a storage tank of the cartridge may be at least partially received within the cavity of the control body while a mouthpiece of the cartridge remains exposed outside of the cavity of the control body. The cartridge may be retained within the cavity formed by the control body housing, such as by an interference fit (e.g., through use of detents and/or other features creating an interference engagement between an outer surface of the cartridge and an interior surface of a wall forming the control body cavity), by a magnetic engagement (e.g., though use of magnets and/or magnetic metals positioned within the cavity of the control body and positioned on the cartridge), or by other suitable techniques.

As seen in the cut-away view illustrated in FIG. 2, the control body 102 and cartridge 104 each include a number of respective components. The components illustrated in FIG. 2 are representative of the components that may be present in a control body and cartridge and are not intended to limit the scope of components that are encompassed by the present disclosure. As shown, for example, the control body can be formed of a housing 206 (sometimes referred to as a control body shell) that can include a control component 208 (e.g., processing circuitry, etc.), a flow sensor 210, a power source 212 (e.g., battery, supercapacitor), and an indicator 214 (e.g., LED, quantum dot-based LED), and such components can be variably aligned. The power source may be rechargeable, and the control component may include a switch and processing circuitry coupled to the flow sensor and the switch. The processing circuitry may be configured to prevent access (lock) the device depending on the age verification status.

The cartridge 104 can be formed of a housing 216 (sometimes referred to as the cartridge shell) enclosing a reservoir 218 configured to retain the aerosol precursor composition, and including a heating element 220 (aerosol production component). In various configurations, this structure may be referred to as a tank; and accordingly, the terms "cartridge," "tank" and the like may be used interchangeably to refer to a shell or other housing enclosing a reservoir for aerosol precursor composition, and including a heating element.

As shown, in some examples, the reservoir 218 may be in fluid communication with a liquid transport element 222 adapted to wick or otherwise transport an aerosol precursor composition stored in the reservoir housing to the heating element 220. In some examples, a valve may be positioned between the reservoir and heating element, and configured to control an amount of aerosol precursor composition passed or delivered from the reservoir to the heating element.

Various examples of materials configured to produce heat when electrical current is applied therethrough may be employed to form the heating element 220. The heating element in these examples may be a resistive heating element such as a wire coil, micro heater or the like. Example materials from which the heating element may be formed include Kanthal (FeCrAl), nichrome, nickel, stainless steel, indium tin oxide, tungsten, molybdenum disilicide (MoSi2), molybdenum silicide (MoSi), molybdenum disilicide doped with aluminum (Mo(Si,Al)2), titanium, platinum, silver, palladium, alloys of silver and palladium, graphite and graphite-based materials (e.g., carbon-based foams and yarns), conductive inks, boron doped silica, and ceramics (e.g., positive or negative temperature coefficient ceramics). The heating element may be resistive heating element or a heating element configured to generate heat through induction. The heating element may be coated by heat conductive ceramics such as aluminum nitride, silicon carbide, beryllium oxide, alumina, silicon nitride, or their composites. Example implementations of heating elements useful in aerosol delivery devices according to the present disclosure are further described below, and can be incorporated into devices such as those described herein.

An opening 224 may be present in the housing 216 (e.g., at the mouth end) to allow for egress of formed aerosol from the cartridge 104.

The cartridge 104 also may include one or more electronic components 226, which may include an integrated circuit, a memory component (e.g., EEPROM, flash memory), a sensor, or the like. The electronic components may be adapted to communicate with the control component 208 and/or with an external device by wired or wireless means. The electronic components may be positioned anywhere within the cartridge or a base 228 thereof.

Although the control component 208 and the flow sensor 210 are illustrated separately, it is understood that various electronic components including the control component and the flow sensor may be combined on a circuit board (e.g., PCB) that supports and electrically connects the electronic components. Further, the circuit board may be positioned horizontally relative the illustration of FIG. 1 in that the circuit board can be lengthwise parallel to the central axis of the control body. In some examples, the air flow sensor may comprise its own circuit board or other base element to which it can be attached. In some examples, a flexible circuit board may be utilized. A flexible circuit board may be configured into a variety of shapes, include substantially tubular shapes. In some examples, a flexible circuit board may be combined with, layered onto, or form part or all of a heater substrate.

The control body 102 and the cartridge 104 may include components adapted to facilitate a fluid engagement therebetween. As illustrated in FIG. 2, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the power source 212 and control component 208 in the control body and the heating element 220 in the cartridge. Further, the housing 206 can include an air intake 236, which may be a notch in the housing where it connects to the coupler that allows for passage of ambient air around the coupler and into the housing where it then passes through the cavity 232 of the coupler and into the cartridge through the projection 234.

A coupler and a base useful according to the present disclosure are described in U.S. Pat. App. Pub. No. 2014/0261495 to Novak et al., which is incorporated herein by reference. For example, the coupler 230 as seen in FIG. 2 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The reservoir 218 illustrated in FIG. 2 can be a container or can be a fibrous reservoir, as presently described. For example, the reservoir can comprise one or more layers of nonwoven fibers substantially formed into the shape of a tube encircling the interior of the housing 216, in this example. An aerosol precursor composition can be retained in the reservoir. Liquid components, for example, can be sorptively retained by the reservoir. The reservoir can be in fluid connection with the liquid transport element 222. The liquid transport element can transport the aerosol precursor composition stored in the reservoir via capillary action—or via a micro pump—to the heating element 220 that is in the form of a metal wire coil in this example. As such, the heating element is in a heating arrangement with the liquid transport element.

In some examples, a microfluidic chip may be embedded in the reservoir 218, and the amount and/or mass of aerosol precursor composition delivered from the reservoir may be controlled by a micro pump, such as one based on microelectromechanical systems (MEMS) technology. Other example implementations of reservoirs and transport elements useful in aerosol delivery devices according to the present disclosure are further described herein, and such reservoirs and/or transport elements can be incorporated into devices such as those described herein. In particular, specific combinations of heating members and transport elements as further described herein may be incorporated into devices such as those described herein.

In use, when a user draws on the aerosol delivery device 100, airflow is detected by the flow sensor 210, and the heating element 220 is activated to vaporize components of the aerosol precursor composition. Drawing upon the mouth end of the aerosol delivery device causes ambient air to enter the air intake 236 and pass through the cavity 232 in the coupler 230 and the central opening in the projection 234 of the base 228. In the cartridge 104, the drawn air combines with the formed vapor to form an aerosol. The aerosol is whisked, aspirated or otherwise drawn away from the heating element and out the opening 224 in the mouth end of the aerosol delivery device.

For further detail regarding implementations of an aerosol delivery device including a control body and a cartridge in the case of an electronic cigarette, see the above-cited U.S. patent application Ser. No. 15/836,086 to Sur; and U.S. patent application Ser. No. 15/916,834 to Sur et al.; as well as U.S. Pat. App. Ser. No. 15/916,696 to Sur, filed Mar. 9, 2018, which is also incorporated herein by reference.

FIGS. 3-6 illustrate implementations of an aerosol delivery device including a control body and an aerosol source member in the case of a heat-not-burn device. More specifically, FIG. 3 illustrates an aerosol delivery device 300 according to an example implementation of the present disclosure. The aerosol delivery device may include a control body 302 and an aerosol source member 304. In various implementations, the aerosol source member and the control body can be permanently or detachably aligned in a functioning relationship. In this regard, FIG. 3 illustrates the aerosol delivery device in a coupled configuration, whereas FIG. 4 illustrates the aerosol delivery device in a decoupled configuration.

As shown in FIG. 4, in various implementations of the present disclosure, the aerosol source member 304 may comprise a heated end 406, which is configured to be inserted into the control body 302, and a mouth end 408, upon which a user draws to create the aerosol. In various implementations, at least a portion of the heated end may include an aerosol precursor composition 410.

In various implementations, the aerosol source member 304, or a portion thereof, may be wrapped in an exterior overwrap material 412, which may be formed of any material useful for providing additional structure and/or support for the aerosol source member. In various implementations, the exterior overwrap material may comprise a material that resists transfer of heat, which may include a paper or other fibrous material, such as a cellulose material. The exterior overwrap material may also include at least one filler material imbedded or dispersed within the fibrous material. In various implementations, the filler material may have the form of water insoluble particles. Additionally, the filler material may incorporate inorganic components. In various implementations, the exterior overwrap may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. The exterior overwrap may also include a material typically used in a filter element of a conventional cigarette, such as cellulose acetate.

Further, an excess length of the overwrap at the mouth end 408 of the aerosol source member may function to simply separate the aerosol precursor composition 410 from the mouth of a consumer or to provide space for positioning of a filter material, as described below, or to affect draw on the article or to affect flow characteristics of the vapor or aerosol leaving the device during draw. Further discussion relating to the configurations for overwrap materials that may be used with the present disclosure may be found in the above-cited U.S. Pat. No. 9,078,473 to Worm et al.

In various implementations other components may exist between the aerosol precursor composition 410 and the mouth end 408 of the aerosol source member 304, wherein the mouth end may include a filter 414, which may, for example, be made of a cellulose acetate or polypropylene material. The filter may additionally or alternatively contain strands of tobacco containing material, such as described in U.S. Pat. No. 5,025,814 to Raker et al., which is incorporated herein by reference in its entirety. In various implementations, the filter may increase the structural integrity of the mouth end of the aerosol source member, and/or provide filtering capacity, if desired, and/or provide resistance to draw. In some implementations one or any combination of the following may be positioned between the aerosol precursor composition and the mouth end: an air gap; phase change materials for cooling air; flavor releasing media; ion exchange fibers capable of selective chemical adsorption; aerogel particles as filter medium; and other suitable materials.

Various implementations of the present disclosure employ one or more conductive heating elements to heat the aerosol precursor composition 410 of the aerosol source member 304. In various implementations, the heating element may be provided in a variety forms, such as in the form of a foil, a foam, a mesh, a hollow ball, a half ball, discs, spirals, fibers, wires, films, yarns, strips, ribbons, or cylinders. Such heating elements often comprise a metal material and are configured to produce heat as a result of the electrical resistance associated with passing an electrical current therethrough. Such resistive heating elements may be positioned in direct contact with, or in proximity to, the aerosol source member and particularly, the aerosol precursor composition of the aerosol source member. The heating element may be located in the control body and/or the aerosol source member. In various implementations, the aerosol precursor composition may include components (i.e., heat conducting constituents) that are imbedded in, or otherwise part of, the substrate portion that may serve as, or facilitate the function of, the heating assembly. Some examples of various heating members and elements are described in U.S. Pat. No. 9,078,473 to Worm et al.

Some non-limiting examples of various heating element configurations include configurations in which a heating element is placed in proximity with the aerosol source member 304. For instance, in some examples, at least a portion of a heating element may surround at least a portion of an aerosol source member. In other examples, one or more heating elements may be positioned adjacent an exterior of an aerosol source member when inserted in the control body 302. In other examples, at least a portion of a heating element may penetrate at least a portion of an aerosol source member (such as, for example, one or more prongs and/or spikes that penetrate an aerosol source member), when the aerosol source member is inserted into the control body. In some instances, the aerosol precursor composition may include a structure in contact with, or a plurality of beads or particles imbedded in, or otherwise part of, the aerosol precursor composition that may serve as, or facilitate the function of the heating element.

FIG. 5 illustrates a front view of an aerosol delivery device 300 according to an example implementation of the present disclosure, and FIG. 6 illustrates a sectional view through the aerosol delivery device of FIG. 5. In particular, the control body 302 of the depicted implementation may comprise a housing 516 that includes an opening 518 defined in an engaging end thereof, a flow sensor 520 (e.g., a puff sensor or pressure switch), a control component 522 (e.g., processing circuitry, etc.), a power source 524 (e.g., battery, supercapacitor), and an end cap that includes an indicator 526 (e.g., a LED). The power source may be rechargeable, and the control component may include a switch and processing circuitry coupled to the flow sensor and the switch. The processing circuitry may be configured to prevent operation with the switch if the age verification fails as further discussed below.

In one implementation, the indicator 526 may comprise one or more LEDs, quantum dot-based LEDs or the like. The indicator can be in communication with the control component 522 and be illuminated, for example, when a user draws on the aerosol source member 304, when coupled to the control body 302, as detected by the flow sensor 520.

The control body 302 of the depicted implementation includes one or more heating assemblies 528 (individually or collectively referred to a heating assembly) configured to heat the aerosol precursor composition 410 of the aerosol source member 304. Although the heating assembly of various implementations of the present disclosure may take a variety of forms, in the particular implementation depicted in FIGS. 5 and 6, the heating assembly comprises an outer cylinder 530 and a heating element 532 (aerosol production component), which in this implementation comprises a plurality of heater prongs that extend from a receiving base 534 (in various configurations, the heating assembly or more specifically the heater prongs may be referred to as a heater). In the depicted implementation, the outer cylinder comprises a double-walled vacuum tube constructed of stainless steel to maintain heat generated by the heater prongs within the outer cylinder, and more particularly, maintain heat generated by heater prongs within the aerosol precursor composition. In various implementations, the heater prongs may be constructed of one or more conductive materials, including, but not limited to, copper, aluminum, platinum, gold, silver, iron, steel, brass, bronze, graphite, or any combination thereof.

As illustrated, the heating assembly 528 may extend proximate an engagement end of the housing 516, and may be configured to substantially surround a portion of the heated end 406 of the aerosol source member 304 that includes the aerosol precursor composition 410. In such a manner, the heating assembly may define a generally tubular configuration. As illustrated in FIGS. 5 and 6, the heating element 532 (e.g., plurality of heater prongs) is surrounded by the outer cylinder 530 to create a receiving chamber 536. In such a manner, in various implementations the outer cylinder may comprise a nonconductive insulating material and/or construction including, but not limited to, an insulating polymer (e.g., plastic or cellulose), glass, rubber, ceramic, porcelain, a double-walled vacuum structure, or any combinations thereof.

In some implementations, one or more portions or components of the heating assembly 528 may be combined with, packaged with, and/or integral with (e.g., embedded within) the aerosol precursor composition 410. For example, in some implementations the aerosol precursor composition may be formed of a material as described above and may include one or more conductive materials mixed therein. In some of these implementations, contacts may be connected directly to the aerosol precursor composition such that, when the aerosol source member is inserted into the receiving chamber of the control body, the contacts make electrical connection with the electrical energy source. Alternatively, the contacts may be integral with the electrical energy source and may extend into the receiving chamber such that, when the aerosol source member is inserted into the receiving chamber of the control body, the contacts make electrical connection with the aerosol precursor composition. Because of the presence of the conductive material in the aerosol precursor composition, the application of power from the electrical energy source to the aerosol precursor composition allows electrical current to flow and thus produce heat from the conductive material. Thus, in some implementations the heating element may be described as being integral with the aerosol precursor composition. As a non-limiting example, graphite or other suitable, conductive material may be mixed with, embedded in, or otherwise present directly on or within the material forming the aerosol precursor composition to make the heating element integral with the medium.

As noted above, in the illustrated implementation, the outer cylinder 530 may also serve to facilitate proper positioning of the aerosol source member 304 when the aerosol source member is inserted into the housing 516. In various implementations, the outer cylinder of the heating assembly 528 may engage an internal surface of the housing to provide for alignment of the heating assembly with respect to the housing. Thereby, as a result of the fixed coupling between the heating assembly, a longitudinal axis of the heating assembly may extend substantially parallel to a longitudinal axis of the housing. In particular, the support cylinder may extend from the opening 518 of the housing to the receiving base 534 to create the receiving chamber 536.

The heated end 406 of the aerosol source member 304 is sized and shaped for insertion into the control body 302. In various implementations, the receiving chamber 536 of the control body may be characterized as being defined by a wall with an inner surface and an outer surface, the inner surface defining the interior volume of the receiving chamber. For example, in the depicted implementations, the outer cylinder 530 defines an inner surface defining the interior volume of the receiving chamber. In the illustrated implementation, an inner diameter of the outer cylinder may be slightly larger than or approximately equal to an outer diameter of a corresponding aerosol source member (e.g., to create a sliding fit) such that the outer cylinder is configured to guide the aerosol source member into the proper position (e.g., lateral position) with respect to the control body. Thus, the largest outer diameter (or other dimension depending upon the specific cross-sectional shape of the implementations) of the aerosol source member may be sized to be less than the inner diameter (or other dimension) at the inner surface of the wall of the open end of the receiving chamber in the control body. In some implementations, the difference in the respective diameters may be sufficiently small so that the aerosol source member fits snugly into the receiving chamber, and frictional forces prevent the aerosol source member from being moved without an applied force. On the other hand, the difference may be sufficient to allow the aerosol source member to slide into or out of the receiving chamber without requiring undue force.

In the illustrated implementation, the control body 302 is configured such that when the aerosol source member 304 is inserted into the control body, the heating element 532 (e.g., heater prongs) is located in the approximate radial center of at least a portion of the aerosol precursor composition 410 of the heated end 406 of the aerosol source member. In such a manner, when used in conjunction with a solid or semi-solid aerosol precursor composition, the heater prongs may be in direct contact with the aerosol precursor composition. In other implementations, such as when used in conjunction with an extruded aerosol precursor composition that defines a tube structure, the heater prongs may be located inside of a cavity defined by an inner surface of the extruded tube structure, and would not contact the inner surface of the extruded tube structure.

During use, the consumer initiates heating of the heating assembly 528, and in particular, the heating element 532 that is adjacent the aerosol precursor composition 410 (or a specific layer thereof). Heating of the aerosol precursor composition releases the inhalable substance within the aerosol source member 304 so as to yield the inhalable substance. When the consumer inhales on the mouth end 408 of the aerosol source member, air is drawn into the aerosol source member through an air intake 538 such as openings or apertures in the control body 302. The combination of the drawn air and the released inhalable substance is inhaled by the consumer as the drawn materials exit the mouth end of the aerosol source member. In some implementations, to initiate heating, the consumer may manually actuate a push-button or similar component that causes the heating element of the heating assembly to receive electrical energy from the battery or other energy source. The electrical energy may be supplied for a pre-determined length of time or may be manually controlled.

In some implementations, flow of electrical energy does not substantially proceed in between puffs on the device 300 (although energy flow may proceed to maintain a baseline temperature greater than ambient temperature—e.g., a temperature that facilitates rapid heating to the active heating temperature). In the depicted implementation, however, heating is initiated by the puffing action of the consumer through use of one or more sensors, such as flow sensor 520. Once the puff is discontinued, heating will stop or be reduced. When the consumer has taken a sufficient number of puffs so as to have released a sufficient amount of the inhalable substance (e.g., an amount sufficient to equate to a typical smoking experience), the aerosol source member 304 may be removed from the control body 302 and discarded. In some implementations, further sensing elements, such as capacitive sensing elements and other sensors, may be used as discussed in U.S. patent application Ser. No. 15/707,461 to Phillips et al., which is incorporated herein by reference.

In various implementations, the aerosol source member 304 may be formed of any material suitable for forming and maintaining an appropriate conformation, such as a tubular shape, and for retaining therein the aerosol precursor composition 410. In some implementations, the aerosol source member may be formed of a single wall or, in other implementations, multiple walls, and may be formed of a material (natural or synthetic) that is heat resistant so as to retain its structural integrity—e.g., does not degrade—at least at a temperature that is the heating temperature provided by the electrical heating element, as further discussed herein. While in some implementations, a heat resistant polymer may be used, in other implementations, the aerosol source member may be formed from paper, such as a paper that is substantially straw-shaped. As further discussed herein, the aerosol source member may have one or more layers associated therewith that function to substantially prevent movement of vapor therethrough. In one example implementation, an aluminum foil layer may be laminated to one surface of the aerosol source member. Ceramic materials also may be used. In further implementations, an insulating material may be used so as not to unnecessarily move heat away from the aerosol precursor composition. Further example types of components and materials that may be used to provide the functions described above or be used as alternatives to the materials and components noted above can be those of the types set forth in U.S. Pat. App. Pub. Nos. 2010/00186757 to Crooks et al., 2010/00186757 to Crooks et al., and 2011/0041861 to Sebastian et al., all of which are incorporated herein by reference.

In the depicted implementation, the control body 302 includes a control component 522 that controls the various functions of the aerosol delivery device 300, including providing power to the electrical heating element 532. For example, the control component may include processing circuitry (which may be connected to further components, as further described herein) that is connected by electrically conductive wires (not shown) to the power source 524. In various implementations, the processing circuitry may control when and how the heating assembly 528, and particularly the heater prongs, receives electrical energy to heat the aerosol precursor composition 410 for release of the inhalable substance for inhalation by a consumer. In some implementations, such control may be activated by a flow sensor 520 as described in greater detail above.

As seen in FIGS. 5 and 6, the heating assembly 528 of the depicted implementation comprises an outer cylinder 530 and a heating element 532 (e.g., plurality of heater prongs) that extend from a receiving base 534. In some implementations, such as those wherein the aerosol precursor composition 410 comprises a tube structure, the heater prongs may be configured to extend into a cavity defined by the inner surface of the aerosol precursor composition. In other implementations, such as the depicted implementation wherein the aerosol precursor composition comprises a solid or semi-solid, the plurality of heater prongs are configured to penetrate into the aerosol precursor composition contained in the heated end 406 of the aerosol source member 304 when the aerosol source member is inserted into the control body 302. In such implementations, one or more of the components of the heating assembly, including the heater prongs and/or the receiving base, may be constructed of a non-stick or stick-resistant material, for example, certain aluminum, copper, stainless steel, carbon steel, and ceramic materials. In other implementations, one or more of the components of the heating assembly, including the heater prongs and/or the receiving base, may include a non-stick coating, including, for example, a polytetrafluoroethylene (PTFE) coating, such as Teflon®, or other coatings, such as a stick-resistant enamel coating, or a ceramic coating, such as Greblon®, or Thermolon™, or a ceramic coating, such as Greblon®, or Thermolon™.

In addition, although in the depicted implementation there are multiple heater prongs 532 that are substantially equally distributed about the receiving base 534, it should be noted that in other implementations, any number of heater prongs may be used, including as few as one, with any other suitable spatial configuration. Furthermore, in various implementations the length of the heater prongs may vary. For example, in some implementations the heater prongs may comprise small projections, while in other implementations the heater prongs may extend any portion of the length of the receiving chamber 536, including up to about 25%, up to about 50%, up to about 75%, and up to about the full length of the receiving chamber. In still other implementations, the heating assembly 528 may take on other configurations. Examples of other heater configurations that may be adapted for use in the present invention per the discussion provided above can be found in U.S. Pat. No. 5,060,671 to Counts et al., U.S. Pat. No. 5,093,894 to Deevi et al., U.S. Pat. No. 5,224,498 to Deevi et al., U.S. Pat. No. 5,228,460 to Sprinkel Jr., et al., U.S. Pat. No. 5,322,075 to Deevi et al., U.S. Pat. No. 5,353,813 to Deevi et al., U.S. Pat. No. 5,468,936 to Deevi et al., U.S. Pat. No. 5,498,850 to Das, U.S. Pat. No. 5,659,656 to Das, U.S. Pat. No. 5,498,855 to Deevi et al., U.S. Pat. No. 5,530,225 to Hajaligol, U.S. Pat. No. 5,665,262 to Hajaligol, and U.S. Pat. No. 5,573,692 to Das et al.; and U.S. Pat. No. 5,591,368 to Fleischhauer et al., which are incorporated herein by reference.

In various implementations, the control body 302 may include an air intake 538 (e.g., one or more openings or apertures) therein for allowing entrance of ambient air into the interior of the receiving chamber 536. In such a manner, in some implementations the receiving base 534 may also include an air intake. Thus, in some implementations when a consumer draws on the mouth end of the aerosol source member 304, air can be drawn through the air intake of the control body and the receiving base into the receiving chamber, pass into the aerosol source member, and be drawn through the aerosol precursor composition 410 of the aerosol source member for inhalation by the consumer. In some implementations, the drawn air carries the inhalable substance through the optional filter 414 and out of an opening at the mouth end 408 of the aerosol source member. With the heating element 532 positioned inside the aerosol precursor composition, the heater prongs may be activated to heat the aerosol precursor composition and cause release of the inhalable substance through the aerosol source member.

As described above with reference to FIGS. 5 and 6 in particular, various implementations of the present disclosure employ a conductive heater to heat the aerosol precursor composition 410. As also indicated above, various other implementations employ an induction heater to heat the aerosol precursor composition. In some of these implementations, the heating assembly 528 may be configured as an induction heater that comprises a transformer with an induction transmitter and an induction receiver. In implementations in which the heating assembly is configured as the induction heater, the outer cylinder 530 may be configured as the induction transmitter, and the heating element 532 (e.g., plurality of heater prongs) that extend from the receiving base 534 may be configured as the induction receiver. In various implementations, one or both of the induction transmitter and induction receiver may be located in the control body 302 and/or the aerosol source member 304.

In various implementations, the outer cylinder 530 and heating element 532 as the induction transmitter and induction receiver may be constructed of one or more conductive materials, and in further implementations the induction receiver may be constructed of a ferromagnetic material including, but not limited to, cobalt, iron, nickel, and combinations thereof. In one example implementation, the foil material is constructed of a conductive material and the heater prongs are constructed of a ferromagnetic material. In various implementations, the receiving base may be constructed of a non-conductive and/or insulating material.

The outer cylinder 530 as the induction transmitter may include a laminate with a foil material that surrounds a support cylinder. In some implementations, the foil material may include an electrical trace printed thereon, such as, for example, one or more electrical traces that may, in some implementations, form a helical coil pattern when the foil material is positioned around the heating element 532 as the induction receiver. The foil material and support cylinder may each define a tubular configuration. The support cylinder may be configured to support the foil material such that the foil material does not move into contact with, and thereby short-circuit with, the heater prongs. In such a manner, the support cylinder may comprise a nonconductive material, which may be substantially transparent to an oscillating magnetic field produced by the foil material. In various implementations, the foil material may be imbedded in, or otherwise coupled to, the support cylinder. In the illustrated implementation, the foil material is engaged with an outer surface of the support cylinder; however, in other implementations, the foil material may be positioned at an inner surface of the support cylinder or be fully imbedded in the support cylinder.

The foil material of the outer cylinder 530 may be configured to create an oscillating magnetic field (e.g., a magnetic field that varies periodically with time) when alternating current is directed through it. The heater prongs of the heating element 532 may be at least partially located or received within the outer cylinder and include a conductive material. By directing alternating current through the foil material, eddy currents may be generated in the heater prongs via induction. The eddy currents flowing through the resistance of the material defining the heater prongs may beat it by Joule heating (i.e., through the Joule effect). The heater prongs may be wirelessly heated to form an aerosol from the aerosol precursor composition 410 positioned in proximity to the heater prongs.

Other implementations of the aerosol delivery device, control body and aerosol source member are described in the above-cited U.S. patent application Ser. No. 15/916,834 to Sur et al.; U.S. patent application Ser. No. 15/916,696 to Sur; and U.S. patent application Ser. No. 15/836,086 to Sur.

FIGS. 7 and 8 illustrate implementations of an aerosol delivery device including a control body and a cartridge in the case of a no-heat-no-burn device. In this regard, FIG. 7 illustrates a side view of an aerosol delivery device 700 including a control body 702 and a cartridge 704, according to various example implementations of the present disclosure. In particular, FIG. 7 illustrates the control body and the cartridge coupled to one another. The control body and the cartridge may be detachably aligned in a functioning relationship.

FIG. 8 more particularly illustrates the aerosol delivery device 700, in accordance with some example implementations. As seen in the cut-away view illustrated therein, again, the aerosol delivery device can comprise a control body 702 and a cartridge 704 each of which include a number of respective components. The components illustrated in FIG. 8 are representative of the components that may be present in a control body and cartridge and are not intended to limit the scope of components that are encompassed by the present disclosure. As shown, for example, the control body can be formed of a control body housing or shell 806 that can include a control component 808 (e.g., processing circuitry, etc.), an input device 810, a power source 812 and an indicator 814 (e.g., LED, quantum dot-based LED), and such components can be variably aligned. Here, a particular example of a suitable control component includes the PIC16 (L)F1713/6 microcontrollers from Microchip Technology Inc., which is described in Microchip Technology, Inc., AN2265, Vibrating Mesh Nebulizer Reference Design (2016), which is incorporated by reference.

The cartridge 704 can be formed of a housing—referred to at times as a cartridge shell 816—enclosing a reservoir 818 configured to retain the aerosol precursor composition, and including a nozzle 820 having a piezoelectric/piezomagnetic mesh (aerosol production component). Similar to above, in various configurations, this structure may be referred to as a tank.

The reservoir 818 illustrated in FIG. 8 can be a container or can be a fibrous reservoir, as presently described. The reservoir may be in fluid communication with the nozzle 820 for transport of an aerosol precursor composition stored in the reservoir housing to the nozzle. An opening 822 may be present in the cartridge shell 816 (e.g., at the mouthend) to allow for egress of formed aerosol from the cartridge 704.

In some examples, a transport element may be positioned between the reservoir 818 and nozzle 820, and configured to control an amount of aerosol precursor composition passed or delivered from the reservoir to the nozzle. In some examples, a microfluidic chip may be embedded in the cartridge 704, and the amount and/or mass of aerosol precursor composition delivered from the reservoir may be controlled by one or more microfluidic components. One example of a microfluidic component is a micro pump 824, such as one based on microelectromechanical systems (MEMS) technology. Examples of suitable micro pumps include the model MDP2205 micro pump and others from thinXXS Microtechnology AG, the mp5 and mp6 model micro pumps and others from Bartels Mikrotechnik GmbH, and piezoelectric micro pumps from Takasago Fluidic Systems.

As also shown, in some examples, a micro filter 826 may be positioned between the micro pump 824 and nozzle 820 to filter aerosol precursor composition delivered to the nozzle. Like the micro pump, the micro filter is a microfluidic component. Examples of suitable micro filters include flow-through micro filters those manufactured using lab-on-a-chip (LOC) techniques.

In use, when the input device 810 detects user input to activate the aerosol delivery device, the piezoelectric/piezomagnetic mesh is activated to vibrate and thereby draw aerosol precursor composition through the mesh. This forms droplets of aerosol precursor composition that combine with air to form an aerosol. The aerosol is whisked, aspirated or otherwise drawn away from the mesh and out the opening 822 in the mouthend of the aerosol delivery device.

The aerosol delivery device 700 can incorporate the input device 810 such as a switch, sensor or detector for control of supply of electric power to the piezoelectric/piezomagnetic mesh of the nozzle 820 when aerosol generation is desired (e.g., upon draw during use). As such, for example, there is provided a manner or method of turning off power to the mesh when the aerosol delivery device is not being drawn upon during use, and for turning on power to actuate or trigger the production and dispensing of aerosol from the nozzle during draw. Additional representative types of sensing or detection mechanisms, structure and configuration thereof, components thereof, and general methods of operation thereof, are described above and in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference.

For more information regarding the above and other implementations of an aerosol delivery device in the case of a no-heat-no-burn device, see U.S. patent application Ser. No. 15/651,548 to Sur., filed Jul. 17, 2017, which is incorporated herein by reference.

As described above, the aerosol delivery device of example implementations may include various electronic components in the context of an electronic cigarette, heat-not-burn device or no-heat-no-burn device, or even in the case of a device that includes the functionality of one or more of an electronic cigarette, heat-not-burn device or no-heat-no-burn device. FIG. 9 illustrates a circuit diagram of an aerosol delivery device 900 that may be or incorporate functionality of any one or more of aerosol delivery devices 100, 300, 700 according to various example implementations of the present disclosure.

As shown in FIG. 9, the aerosol delivery device 900 includes a control body 902 with a power source 904 and a control component 906 that may correspond to or include functionality of respective ones of the control body 102, 302, 702, power source 212, 524, 812, and control component 208, 522, 808. The aerosol delivery device also includes an aerosol production component 916 that may correspond to or include functionality of heating element 220, 532, or piezoelectric/piezomagnetic mesh of nozzle 820. The control body 902 may include the aerosol production component 916 or terminals 918 configured to connect the aerosol production component to the control body.

In some implementations, the control body 902 includes a sensor 908 configured to produce measurements of air flow. The sensor 908 may correspond to or include functionality of the flow sensor 210, 520 or input device 810. In these implementations, the control component 906 includes a switch 910 coupled to and between the power source 904 and the aerosol production component 916. The control component also includes processing circuitry 912 coupled to the sensor and the switch. The switch can be a Metal Oxide Semiconductor Field Effect Transistor (MOSFET) switch. The sensor may be connected to inter-integrated circuit (I2C), Vcc and/or ground of the processing circuitry.

In some implementations, the processing circuitry 912 is configured to verify the age of a user, and to output a signal (as indicated by arrow 922) to cause the switch 910 to switchably connect and disconnect an output voltage from the power source 904 to the aerosol production component 916 to power the aerosol production component for an aerosol-production time period. In some implementations, the processing circuitry is configured to output a pulse width modulation (PWM) signal. A duty cycle of the PWM signal is adjustable to cause the switch to switchably connect and disconnect the output voltage to the aerosol production component. The age verification and authentication process may be used to determine when the connection is made. If the user is not verified or authenticated, the switch may be disconnected to prevent voltage being provided to the aerosol production component. Alternatively, if the switch is in a disconnected state, then if the user is not verified or authenticated, the switch will remain in a disconnected state. Likewise, when the user is verified or authenticated, switch can establish a connection so that current will be able flow from the charging accessory to the device. In other words, when the user is verified or authenticated, the output voltage is permitted to be provided to the aerosol production component.

The aerosol production component 916 may be controlled in a number of different manners, including via the power provided to the aerosol production component during the aerosol-production time period. In some implementations, at a periodic rate during the aerosol-production time period, the processing circuitry 912 is configured to determine a sample window of measurements of instantaneous actual power provided to the aerosol production component. Each measurement of the sample window of measurements may be determined as a product of a voltage at and a current through the aerosol production component. The processing circuitry of such implementations may be further configured to calculate a moving average power provided to the aerosol production component based on the sample window of measurements of instantaneous actual power. In such implementations, the processing circuitry may be further configured to compare the moving average power to a power set point, and output the signal to cause the switch to respectively disconnect and connect the output voltage at each instance in which the moving average power is respectively above or below the power set point. In one example, the processing circuitry 912 can determine the actual voltage and current (I) through the aerosol production component 916. The processing circuitry can read the determined voltage and current values from analog to digital converter (ADC) inputs of the processing circuitry and determine an instantaneous "actual" power (I*V) directed to the aerosol production component. In some instances, such an "instantaneous" power measurement may be added to a sample window or moving window of values (i.e., other instantaneous power measurements) and then a moving average power of the sample window may be calculated, for example, according to the equation, $P_{avg}=P_{sample}+P_{avg}^{1}/$ WindowSize. In some aspects, for example, the window size may be between about 20 and about 256 samples.

in some examples, the processing circuitry 912 may then compare the calculated moving average power to a power set point. The power set point can be a selected power set point associated with the power source 904 (e.g., a power level or current output from the power source regulated by the processing circuitry 912, or other regulating component associated therewith and disposed in electrical communication between the power source and the aerosol production component 916).

In some examples, (1) if $P_{ave}$ (the actual power determined at the aerosol production component 916) is below the selected power set point (the average power), the switch 910 is turned on so as to allow current flow from the power source 904 to the aerosol production component; (2) if $P_{ave}$ is above the selected power set point, the switch is turned off so as to prevent current flow from the power source to the aerosol production component; and (3) steps 1 and 2 are repeated until expiration or cessation of the aerosol-production time period. More particularly, during the aerosol-production time period, the determination and calculation of the actual power at the aerosol production component, the comparison of the actual power to the pre-selected power set point, and ON/OFF decisions for the switch to adjust the pre-selected power set point may be substantially continuously performed by the processing circuitry 912 at a periodic rate, for example, of between about 20 and 50 times per second, so as to ensure a more stable and accurate average power directed to and delivered at the aerosol production component. Various examples of controlling the switch based on the actual power determined at the aerosol production component (Pave) are described in U.S. Pat. No. 9,423,152 to Ampolini et al., which is incorporated herein by reference.

Although not shown, the processing circuitry 912 and/or the signal conditioning circuitry 914 may be coupled with or receive a signal from a charging accessory for authentication or verification. If the verification or authentication signal is received and correct, then the processing circuitry 912 may turn on the switch 910 to allow operation of the aerosol delivery device. Alternatively or in addition, if the verification signal is not received or not correct, then the processing circuitry 912 may shut off the switch 910 to prevent operation of the aerosol delivery device 900. The example communication between the charging accessory and the control body 902 is further illustrated in, and described with reference to FIGS. 14 and 18. The charging accessory may be in communication with the control body 902 and specifically with the processing circuitry 912 and/or the signal conditioning circuitry 914 for controlling the switch 910. In other words, the charger accessory provides authentication or verification (e.g. minimum age) on behalf of the aerosol delivery device 900 and the control body 902 (through the switch 910) can prevent usage. In an alternative embodiment, the sensor 908 may be in communication with the charging accessory. U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; and U.S. Pat. No. 8,689,804 to Fernando et al. discloses identification systems for smoking devices; all of the foregoing disclosures being incorporated herein by reference.

In some implementations, the control component 906 further includes signal conditioning circuitry 914 coupled to the sensor 908 and the processing circuitry 912. The signal conditioning circuitry of such implementations may be configured to manipulate the operation of the switch 910. The signal conditioning circuitry will be described in greater detail below with reference to FIG. 10.

FIG. 10 illustrates a circuit diagram of signal conditioning circuitry 1000 that may correspond to signal conditioning circuitry 914, according to an example implementation of the present disclosure. As shown, in some implementations, the signal conditioning circuitry 1000 includes a signal conditioning chip 1001, and a bidirectional voltage-level translator 1002. One example of a suitable signal conditioning chip is the model ZAP 3456 from Zap-Tech corporation. And one example of a suitable bidirectional voltage-level translator is the model NVT 2003 bidirectional voltage-level translator from NXP Semiconductors.

In one example, as shown in FIG. 10, the signal conditioning chip 1001 can be connected to the bidirectional voltage-level translator 1002, and the bidirectional voltage-level translator can be connected to the 5V input and ground of the processing circuitry 912. Note that the values (e.g., voltage, resistances and capacitance) shown in FIG. 10 are for purposes of illustrating the example only, and unless stated otherwise, the values should not be taken as limiting in the present disclosure.

FIG. 11a and FIG. 111b illustrate example system diagrams with an accessory 1104. FIG. 11a illustrate a power flow 1110 portion of the system and FIG. 11b illustrates a verification 1112 portion. The accessory 1104 may be referred to as a charging accessory or a charger and connects with a device 1106. The device 1106 may be any electronic nicotine delivery systems ("ENDS") device including an aerosol delivery device as described above. The accessory 1104 may couple with a power supply 1108 to provide power to the device 1106 as shown in FIG. 11a. The power supply 1108 can be any power providing mechanism, such as a power outlet, or another device that provides power such as a computer, laptop, mobile device, phone, tablet, or a wireless power source.

FIG. 11b illustrates the verification 1112 by which the accessory 1104 communicates with the age verification system 1102 in order to verify the user's age, which may also be used to authenticate the device 1106 periodically. As described, the age verification system 1102 may not only verify an age (e.g. for an age restricted product), but may also provide authentication or user identification (e.g. for an actual purchase or to prevent theft). The authentication described below may rely on age verification being performed first and then referenced for subsequent authentication. However, there may be other verification mechanisms other than just for age. For example, in some embodiments, user identification may be performed in lieu of age verification. The age verification system 1102 is further described with reference to FIG. 17.

FIG. 12 illustrates example charging accessories 1104, which may be any type of recharging technology. Examples of suitable chargers include chargers that simply supply constant or pulsed direct current (DC) power to the power source, fast chargers that add control circuitry, three-stage chargers, induction-powered chargers, smart chargers, motion-powered chargers, pulsed chargers, solar chargers, USB-based chargers and the like. The charger may include a wireless charger that does not require contact to charge and that charge over a distance and have similar range to Wi-Fi or Bluetooth, in one example, and transmit energy over the air. Example wireless chargers include those using technologies available from POWERCAST, OSSIA, and ENERGUS. The device 1106 may include any of a number of different terminals, electrical connectors or the like to connect with the charging accessory 1104, and in some examples, to connect to other peripherals for communication.

A charging cable 1206 may connect the device 1106 with the power supply 1108. The charging cable 1206 may include authentication circuitry as further discussed below with respect to FIG. 13. The charging cable 1206 may include one or more connectors that are configured to provide power to and/or communicate with the device 1106. Example connectors include direct current (DC) connectors such as cylindrical connectors, cigarette lighter connectors and USB connectors including those specified by USB 1.x (e.g., Type A, Type B), USB 2.0 and its updates and additions (e.g., Mini A, Mini B, Mini AB, Micro A, Micro B, Micro AB) and USB 3.x (e.g., Type A, Type B, Micro B, Micro AB, Type C), future USB versions, proprietary connectors such as Apple's Lightning connector, and the like. The control body 902 of the device 1106 may directly connect with the power supply 1108 (with a built-in charging accessory 1104), or the two may connect via the charging cable 1206 that has suitable connectors. For the charging cable 1206, the control body of the device 1106 and may have the same or different type of connector with the charging cable 1206 having a matching type of connector.

The charging accessory 1104 may be a charging case 1208, which may also be referred to as a carrying case. The charging case 1208 may include its own power source or battery (e.g. battery 1312 in FIG. 13 discussed below) for charging the device 1106. In some embodiments, the charging case 1208 may hold and/or charge multiple devices 1106 at one time. The charging case 1208 itself may be connected to a separate power source or recharging technology for charging its battery. The charging case 1208 may include a cradle, dock, sleeve or the like. More specifically, for example, the control body 902 of the device 1106 may be configured to engage a cradle that includes a USB connector to connect to a power supply (e.g. power supply 1108). In another example, the control body 902 of the device 1106 may be configured to fit within and engage a sleeve that includes a USB connector to connect to a power supply. In these and similar examples, the USB connector may connect directly to the power source, or the USB connector may connect to the power source via a suitable power adapter.

The charging accessory 1104 may be an adapter 1210, which may be referred to as a power adapter. In some examples, the charging accessory 1104 includes the power adapter 1210 and any suitable charge circuitry (e.g. the authentication circuitry from FIG. 13). In other examples, the charger includes the power adapter and the device (e.g. device 1106) is equipped with charge circuitry. In these other examples, the charging accessory 1104 may be simply referred to as a power adapter 1210. The adapter may be a wall wart that is plugged into a power outlet in the wall and which is proprietarily connected to a charging cable that is used to deliver current to the device. The wall wart could be generic such that the charging cable includes the necessary age verification functionality, or that functionality could be located on the wall wart and the charging cable is generic. Alternatively, the functionality could be split between the wall wart and the cable.

The charging accessory 1104 may be wireless 1212. An example of a wireless 1212 charging accessory includes a wireless pad, which may rely on inductive charging to wirelessly charge the device 1106. For induction-powered charging, the device 1106 may be equipped with inductive wireless charging technology and include an induction receiver to connect with a wireless charger, charging pad or the like that includes an induction transmitter and uses inductive wireless charging (including for example, wireless charging according to the Qi wireless charging standard from the Wireless Power Consortium (WPC)). Rather than a pad, the charging accessory 1104 may be a wireless radio frequency (RF) based charger. An example of an inductive wireless charging system is described in U.S. Pat. App. Pub. No. 2017/0112196 to Sur et al., which is incorporated herein by reference in its entirety. Further, in some implementations in the case of an electronic cigarette, the cartridge may comprise a single-use cartridge, as disclosed in U.S. Pat. No. 8,910,639 to Chang et al., which is incorporated herein by reference. An alternative example of a wireless 1212 charging accessory is a wireless block that may have a larger range than the wireless pad and may provide charge in any direction within a certain proximity.

The charging accessory 1104 may be or may include a biometric sensor 1214. The biometrics of a user may be detected and used for verification or authentication of the user as discussed with respect to FIGS. 17a-17b. Example biometrics include fingerprints, facial recognition, iris/eye recognition, blood, or DNA. In one example, the biometric sensor 1214 may be used to periodically re-authenticate a user whose age was already verified. For example, for each new cartridge, a user may be required to apply their fingerprint to the biometric sensor 1214 to authenticate and ensure that another user is not using the already age-verified device. The periodicity of re-authentication can be varied and may be based on time, number of puffs, charges status (e.g. each charging cycle), and/or other triggers. Example authentication examples, including biometrics, are further discussed with respect to FIG. 17b.

FIG. 13 illustrates an embodiment of the charging accessory 1104. The charging accessory 1104 may include circuitry, such as the authentication circuitry 1302 that operates to perform the authentication or may also be used for the initial age verification. The authentication circuitry 1302 may include a processor 1304, a memory 1306, and a switch 1308.

The processor 1304 in the authentication circuitry 1302 may be on one or more chips and may include a central processing unit (CPU), a graphics processing unit (GPU), a digital signal processor (DSP) or other type of processing device. The processor 1304 may be one or more general processors, digital signal processors, application specific integrated circuits, field programmable gate arrays, servers, networks, digital circuits, analog circuits, combinations thereof, or other now known or later developed devices for analyzing and processing data. The processor 1304 may operate in conjunction with a software program, such as code generated manually (i.e., programmed).

The processor 1304 may be coupled with a memory 1306, or the memory 1306 may be a separate component. The memory 1306 may include, but is not limited to, computer readable storage media such as various types of volatile and non-volatile storage media, including random access memory, read-only memory, programmable read-only memory, electrically programmable read-only memory, electrically erasable read-only memory, flash memory, magnetic tape or disk, optical media and the like. The memory 1306 may include a random access memory for the processor 1304. Alternatively, the memory 1306 may be separate from the processor 1304, such as a cache memory of a processor, the system memory, or other memory. The memory 1306 may be an external storage device or database for storing recorded ad or user data. Examples include a hard drive, compact disc ("CD"), digital video disc ("DVD"), memory card, memory stick, floppy disc, universal serial bus ("USB") memory device, or any other device operative to store ad or user data. The memory 1306 is operable to store instructions executable by the processor 1304.

The functions, acts or tasks illustrated in the figures or described herein may be performed by the programmed processor executing the instructions stored in the memory 1306. Specifically, the operation of the age verification system 1102 may be performed by the processor 1304 based on instructions from the memory 1306. The functions, acts or tasks are independent of the particular type of instruction set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

The processor 1304 may be configured to execute software including instructions for verifying a user's age or for subsequent authentication operations for the age verification system 1102. Specifically, if the processor 1304 cannot verify a user's age, then the switch 1308 can be activated to prevent power from a power interface 1310. The power interface 1310 may receive power from a power supply (e.g. the power supply 1108) and/or may power an internal battery 1312. In some embodiments, the charging accessory 1104 may not have a battery, such as when the charging accessory 1104 is the charging cable 1206. In other embodiments such as the charging case 1208, the charging accessory 1104 may be able to charge from its internal battery 1312. The battery 1312 may include any internal power storage component, and may be powered up using a wall plug, USB drive, manual power, battery pack, or any other power source. Once charged to a sufficient level, the charger accessory 1104 may not need to draw separate power in order to unlock (e.g. age verification) and charge the device 1106.

The power interface 1310 may also operate to charge the device 1106 as shown in FIG. 14. The power interface 1310 is configured to interface with both the device 1106 and the power supply (e.g. battery 1312 and/or the power supply 1108). The power interface 1310 may be controlled by the switch 1308 such that the flow of electricity is allowed if authentication from age verification passes. Alternatively, the flow of electricity may be stopped if the authentication or age verification fails. Specifically, the power interface 1310 will not provide electricity to the device 1106 because the switch is turned off. Although the switch 1308 is illustrated as part of the authentication circuitry 1302, it could be a separate component or be part of the power interface 1310 in alternative embodiments.

FIG. 14 illustrates an embodiment showing the connection of the charging accessory 1104 with the device 1106 and the age verification system 1102. The device 1106 may include a battery 1420, which may be the control body discussed above (e.g. 902 in FIG. 9, 302 in FIG. 3-6, or 102 in FIGS. 1-2). The device may further include a cartridge 1422, which may be the cartridge discussed above (e.g. 104 in FIGS. 1-2, 304 in FIGS. 3-6, 704 in FIGS. 7-8, or the aerosol production component 916 in FIG. 9). FIG. 14 illustrates that the power interface 1310 charges the battery 1420 of the device 1106. The power interface 1310 allows the flow of electricity to the battery 1420 if authentication passes. Alternatively, if authentication fails, then the power interface 1310 may prevent the flow of electricity to the battery 1420. The authentication may be a process for verifying a user's identity after that user has already verified their age. Accordingly, if the user does not verify their age, then the authentication process will fail. The age verification process may occur less frequently (e.g. at device purchase) than the authentication process (e.g. each usage, or based on puffs or puff time). In an alternative embodiment, there may be a communication mechanism from the charging accessory 1104 that prevents operation of the device 1106 in ways other than merely preventing the battery 1420 from recharging, such as preventing the cartridge 1422 from receiving electricity needed for heat. In other words, the connection between the charging accessory 1104 may provide a mechanism to lock the device 1106 unless the device is authenticated and the user's age is verified.

The age verification system 1102 provides an indication as to whether a user is of an appropriate age for usage of a particular product, such as an electronic nicotine delivery systems ("ENDS") device including an aerosol delivery device, both of which are examples of the device 1106. At least some components or features of the age verification system 1102 may be part of the charging accessory 1104 or be connected locally to the charging accessory 1104 as shown in FIGS. 11a, 11b, and 14. For example, the processing and determinations from the age verification system 1102 may be performed locally after accessing a remote database. In an alternative embodiment, the age verification system 1102 may be located remotely and accessible over a network as described with reference to FIGS. 15-16.

FIG. 15 illustrates an embodiment of the age verification system 1502 connected over a network 1503. While FIG. 11b illustrated that the charging accessory 1104 was coupled with the age verification system 1102 for authentication, FIG. 15 illustrates an embodiment in which the age verification system 1502 (which may be the same as or different from age verification system 1102) is coupled with the charging accessory 1504 (which may be the same as or different from the charging accessory 1104) over a network 1503.

The present disclosure contemplates a computer-readable medium that includes instructions or receives and executes instructions responsive to a propagated signal, so that a device connected to a network can communicate voice, video, audio, images or any other data over a network. The charging accessory 1504 or the age verification system 1502 may provide the instructions over the network via one or more communication ports. The communication port may be created in software or may be a physical connection in hardware. The connection with the network may be a physical connection, such as a wired Ethernet connection or may be established wirelessly as discussed below. Likewise, the connections with other components may be physical connections or may be established wirelessly. In addition to the charging accessory 1504, the device 1106, and/or the host 1605 (discussed below with respect to FIG. 16) may communicate through a network, including but not limited to the network 1503. For example, the authentication circuitry 1302 may include network functionality in order to be coupled with the age verification system 1102 or 1502. These components may include communication ports configured to connect with a network, such as the network 1503.

The network (e.g. the network 1503) may couple devices so that communications may be exchanged, such as between the charging accessory 1504 and the age verification system 1502, including between other wireless devices coupled via a wireless network, for example. As described a cluster of machines storing data to be analyzed may be connected over one or more networks, such as the network 1503. A network may also include mass storage, such as network attached storage (NAS), a storage area network (SAN), or other forms of computer or machine readable media, for example. A network may include the Internet, one or more local area networks (LANs), one or more wide area networks (WANs), wire-line type connections, wireless type connections, or any combination thereof. Likewise, sub-networks, such as may employ differing architectures or may be compliant or compatible with differing protocols, may interoperate within a larger network. In one example, Blockchain technology may be employed in the network for distributing data over a network. Exemplary Blockchain network functionality is described in the U.S. patent application Ser. No. 16/415,477 filed May 17, 2019, entitled "DECENTRALIZED IDENTITY STORAGE FOR TOBACCO PRODUCTS", which claims priority to U.S. Provisional Pat. App. No. 62/838,272, filed on Apr. 24, 2019, entitled "DECENTRALIZED IDENTITY STORAGE FOR TOBACCO PRODUCTS," the entire disclosures of each of which are incorporated by reference. Various types of devices may, for example, be made available to provide an interoperable capability for differing architectures or protocols. As one illustrative example, a router may provide a link between otherwise separate and independent LANs. A communication link or channel may include, for example, analog telephone lines, such as a twisted wire pair, a coaxial cable, full or fractional digital lines including T1, T2, T3, or T4 type lines, Integrated Services Digital Networks (ISDNs), Digital Subscriber Lines (DSLs), wireless links including satellite links, or other communication links or channels, such as may be known to those skilled in the art. Furthermore, a computing device or other related electronic devices may be remotely coupled to a network, such as via a telephone line or link, for example.

A wireless network may couple devices, such as the charging accessory 1504 (and/or the host 1605 in FIG. 16) and the age verification system 1502. The network 1503 may include a wireless network and may employ stand-alone ad-hoc networks, mesh networks, Wireless LAN (WLAN) networks, wireless wide area network (WWAN), wireless metropolitan area network (WMAN), cellular networks, or the like. A wireless network may further include a system of terminals, gateways, routers, or the like coupled by wireless radio links, or the like, which may move freely, randomly or organize themselves arbitrarily, such that network topology may change, at times even rapidly. A wireless network may further employ a plurality of network access technologies, including Long Term Evolution (LTE), WLAN, Wireless Router (WR) mesh, or 2nd, 3rd, or 4th generation (2G, 3G, 4G, 5G, or future iterations) cellular technology, or the like. A network may enable RF or wireless type communication via one or more network access technologies, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, Zigbee, Z Wave, IEEE 802.16 (e.g., WiMax) and/or other WWAN/WMAN technology, or the like, including future iterations of any of the aforementioned technologies. A wireless network may include virtually any type of wireless communication mechanism by which signals may be communicated between devices, such as the charging accessory 1504 (and/or the host 1605 in FIG. 16) and the age verification system 1502, between or within a network, or the like. In some embodiments, the communication protocols listed above may be used for communication between the charging accessory 1504 and the host 1605, and the host 1605 then communicates with the age verification system 1502 through the same or different communication protocols.

Signal packets communicated via a network, such as the network 1503 or a network of participating digital communication networks, may be compatible with or compliant with one or more protocols. Signaling formats or protocols employed may include, for example, TCP/IP, UDP, DECnet, NetBEUI, IPX, Appletalk, or the like. Versions of the Internet Protocol (IP) may include IPv4 or IPv6. The Internet refers to a decentralized global network of networks. The Internet includes local area networks (LANs), wide area networks (WANs), wireless networks, or long haul public networks that, for example, allow signal packets to be communicated between LANs. Signal packets may be communicated between nodes of a network, such as, for example, to one or more sites employing a local network address. A signal packet may, for example, be communicated over the Internet from a user site via an access node coupled to the Internet. Likewise, a signal packet may be forwarded via network nodes to a target site coupled to the network via a network access node, for example. A signal packet communicated via the Internet may, for example, be routed via a path of gateways, servers, etc. that may route the signal packet in accordance with a target address and availability of a network path to the target address. This signal packet communication may be applicable to the data communication between the charging accessory 1104 and the device 1106 described with respect to FIG. 18, or may be applicable to communications between the charging accessory 1504 (and/or the host 1605 in FIG. 16) and the age verification system 1502.

FIG. 16 illustrates an alternative embodiment of the age verification system 1502 connected with a host 1605 over a network 1503. The host 1605 may be any computing device, such as a smartphone, tablet, or computer. The charging accessory 1504 may couple with the host 1605, which may provide the ability to unlock the charging accessory 1504 if the age verification is satisfied. For example, the charging accessory 1504 may be a cable that connects the host 1605 with the device 1106. In some embodiments, the host 1605 may act as or be the power supply 1108. In other words, there may not be a separate power supply 1108 because the host 1605 can charge the device 1106 through the charging accessory 1504. Specifically, the device 1106 may be charged when the charging accessory 1504 connects the device 1106 with the host 1605. In other embodiments, the host 1605 may provide the functionality for the charging accessory 1504 to communicate over the network 1503 with the age verification system 1502. Although not shown, the coupling of the charging accessory 1504 with the host 1605 may be over a network, such as the network 1503 described above. The host 1605 may be already configured to communicate over a network, such as the network 1503, so the charging accessory 1504 may not need the same level of communication functionality, since the host provides for that capability. In some embodiments, the host 1605 and/or the charging accessory 1504, upon communication with the age verification system 1502, may prevent usage of the device 1106 or prevent further charging of the device 1106.

Although not shown, the device 1106 may be able to directly connect with a network, such as the network 1503. In such an instance, the accessory 1504 would not need a host to connect to the network, or the device 1106 could be considered to be the host. Specifically, the device 1106 may include a network interface (examples described above) and provide the communication over the network 1503 with the age verification system 1502. In one example, the network interface may be WPAN (e.g., Bluetooth) in which case there may still be a host, or the network interface could be WLAN. As an alternative example, both the charging accessory 1504 and the device 1106 could be Bluetooth capable for communication, but the device 1106 may also have WLAN for network communications.

The age verification system 1102, 1502 may include a database that tracks users along with ages. It may be encrypted and/or use anonymous identifiers (e.g. numbers, letters, or any alphanumeric identifiers) for each user. FIG. 17a describes how the initial age verification may occur (e.g. identification documentation 1706) and that may be stored in the database, so all future age verification requests by that user are confirmed. Specifically, once a user is initially age verified as confirmed in the age verification system database, future verifications (i.e. "authentications") may be merely calls to this database for unlocking the device 1106. In other words, a user initially performs an age verification and then subsequent usage may require authentication without the complete initial age verification requirements. The frequency with which the device 1106 must be unlocked or authenticated can vary. Likewise, the timing for when a user needs to re-verify their age may vary. For example, each time the cartridge is replaced, the user may need to re-verify or re-authenticate. In some embodiments, the re-authentication may be required after a certain number of puffs from the device 106 or may be based on the passage of time (e.g. once per hour, day, week, month, etc.). The online database may track the requests for authentication and set limits per user. This can prevent the potential fraud of a single user unlocking other under-age user's devices. This also would prevent the re-distribution of unlocked (i.e. verified and authenticated) charging accessories. Reasonable limits for the number of devices, chargers, and/or authentications can prevent this potential fraud. For example, the limit may be no more than ten charging accessories in a six month period. As noted above, the unlocking that allows usage may be either unlocking of the device 1106 or unlocking of the charging accessory 1104 and may include first the verification of a user's age followed by authentication of that user for each usage. Unlocking of the charging accessory 1104 allows the user to charge a limited number of devices.

FIG. 17a illustrates verification examples 1701 from the age verification system 1102. As described, age verification is a process by which a user's age is verified. The age verification system 1102 provides functionality for verifying the age of a user. The age verification may be for a particular user such that the verification applies for multiple devices used by that user, but may still require authentication for each individual device. In some embodiments, each device may require the age verification process in addition to subsequent authentications. The verification examples 1701 are example mechanisms to verify the user's age. As an initial age verification, the age verification system 1102 may require some identification documentation 1706 to establish the age of a user. For example, a driver's license or passport may be uploaded to establish a user's age. The image from that documentation may be used for future age verification by performing facial recognition 1708 using that image. Facial recognition technology can analyze the two images to either confirm identity match, reject identity verification, or flag the verification to request additional identification information. In alternative embodiments, the verification step may include an audible input from the user, such as recitation of a number, sequence, or code to verify liveliness. Facial recognition may also be used for the authentication process as described below with respect to FIG. 17b. Another verification example 1701 includes a help desk 1707 phone call in which a user can confirm identity by providing or confirming user information. In one embodiment, the help desk 1707 can be used to confirm information provided in the identification document 1706.

FIG. 17b illustrates authentication examples 1702 from the age verification system 1102. The age verification system 1102 provides an indication as to whether a user/device should be authenticated. As described above, the age verification system 1102 may perform age verification in addition to this authentication. The authentication examples 1702 are example mechanisms to either unlock a device or allow charging of that device when a user is authenticated. The authentication may include merely determining an identity of a user and confirming that the user has previously had their age verified. Facial recognition technology 1709 can analyze the two images to either confirm identity match, reject identity authentication, or flag the authentication to request additional identification information. This authentication may include comparing that image to a live self-image ("selfie") or video that the user takes with their mobile device or webcam. This may prevent fraud of merely showing a picture of someone. Specifically, this reduces the potential for using a hard-copy photo to trick the facial recognition software (i.e. holding up the driver's license close to the webcam). The selfie image that the user uploads can also be checked for liveliness by recording a short video to ensure that the frames change. In alternative embodiments, the authentication step may include an audible input from the user, such as recitation of a number, sequence, or code to verify liveliness.

Other authentication examples 1702 include fingerprints 1710. The charger accessory 1104 may include some form of a fingerprint reader for verifying the user after that user has been age verified. In one embodiment, the host 1605 from FIG. 16 may receive the fingerprint that is used for either unlocking the charger accessory 1504 and/or unlocking the device 1106 as part of the authentication process. Other than facial recognition 1709 and fingerprints 1710, there may be other biometrics 1712 that are used for verifying a user, such as DNA, blood, or other biological indicators. Not only may biometrics 1712 be used as part of the authentication process, they may also be used for the age verification process and may be another verification example 1701. Further, the help desk 1707 verification example may also be used as an authentication example 1702 in which a user can authenticate a device by calling the help desk and providing identity information (e.g. name, birth date, social security number, phone number, email, address, and/or a password, such as mother's maiden name).

As a further example, pin codes 1714 may be used for authenticating a user. A pin code may include a password that is associated with the user and used for unlocking the charger accessory 1504 and/or unlocking the device 1106. The pin code may be used to unlock the charging abilities of the product even when the product is not connected to a network. The pin code may include a button in which a certain code must be entered or may include different sensors for detecting a unique interaction. For example, the pin code may further include a puff code in which a pattern of puffing is used for authentication and is measured by a pressure sensor. Further examples of pin codes may include the codes described with respect to FIG. 18.

FIG. 18 illustrates example communications between a charger accessory 1104 and the device 1106. In one example, the pin codes 1714 may include electric pulses 1802 that are communicated between the charger accessory 1104 and the device 1106. When age verification fails, the charging accessory 104 may be in a locked state and will not provide charge to any devices. In one embodiment, the accessory 1104 may communicate with the device 1106.

The data communication 1804 handshake between the device 1106 and the charging accessory 1104 may be proprietary and utilize a data pin connection. Instead of sending current pulses through the charging pins (i.e. electric pulses 1802), in some embodiments, a data package is sent from the device 1106 to the charging accessory 1104 prior to the charger allowing current. Even if the charging accessory 1104 of some embodiments is unlocked, current will not flow into the device 1106 unless the charging accessory 1104 receives the proper data package. The data package can be any number of encryption techniques including, for example, a 128-bit encryption, 192-bit encryption, or 256-bit encryption. In some embodiments, Advance Encryption Standard (AES) techniques may be used In addition, this encryption key can be dynamic where the code changes after a predetermined length of time. The random number generators on the device 1106 and charger may be synced so that they always have matching key codes.

The data communication 1804 may include instructions for unlocking the device 1106 from the charging accessory 1104. This data communication may be wired or wirelessly and utilize communication protocols discussed above, including but not limited to Bluetooth, WiFi, Zigbee, Z wave, or any other wireless communication protocol. The charging accessory 1104 includes a receiver chip internal to a housing that can receive and/or send data. The charging accessory 1104 may communicate with a host (such as a mobile phone) that receives a verification that the user is of proper age from the age verification system online. The host may then transmits data to the charging accessory 1104 via the wireless connection. The charging accessory 1104 may be plugged into a wall or charged to a sufficient level as discussed in alternative embodiments so that the wireless chip is powered for communication. When the charging accessory 1104 receives a correct data or code from the host, it will close a switch (e.g. 910 or 1308) on its internal printed circuit board that allows current to flow from a power supply to the device 1106. If the data code is not correct, or no code is received, then the switch remains open preventing charging from the charging accessory 1104.

The communication may also be through electric pulses 1802, or may include some combination of electric pulses and data/code. Specifically, the electric pulses 1802 may utilize the electronics inherent in the device 1106 and the charger accessory 1104. Specifically, the current sequence from the charging accessory 1104 to the device 1106 may be unique, such as a square wave, sine wave, triangle wave, or other profile of on/off pulses. The device 1106 may be looking for a specific sequence before it allows current to flow from a power source, through the unlocked charger accessory 1104, and into the device 1106 battery. In one embodiment, the electric pulses 1802 may be similar to Morse code communication between the charger 1104 and the device 1106.

The communications shown in FIG. 18 are designed to prevent someone from charging the device 1106 by merely attaching the correct voltage across the charging pins. If the device does not see the correct authentication code (e.g. 15 quick pulses, 5 long pulses, 3 quick pulses, or unique wave), it will determine the power is coming from a malicious or unverified source and will not allow charging. One advantage of using the electric pulses 1802 for communication rather than data communication 1804 is simplicity in that the charger already is capable of providing charge and there would be no need for further functionality (e.g. communication ports, processor, etc.) that may be required for data communication. Although not shown, the communication from the accessory 1104 may also be a power enable/disable command, wherein the disable command is for locking the device when age has not been verified.

FIG. 19 illustrates a connection between a charger accessory 1104 and the device 1106. The charger accessory 1104 may be proprietary in that it only allows specific devices 1106 to be charged. Specifically, the charger accessory 1104 may have a geometric connector 1902 that connects with a corresponding geometric connector 1904 of the device 1106. The geometric connectors may include geometric features that create interference when a disallowed shape or geometry is introduced. For example, a square charger would not allow a round device to be plugged and complete the connection. In other embodiments, there may be a shutter mechanism that blocks access for the complete connection. The shutter mechanism may be similar to child-resistant electrical outlets in which there are springs inside a receptacle that both must be compressed for the shutters to open. Both springs in the outlet are compressed at the same time for the shutters to open. Similar mechanisms may be used for a proprietary connection between the charger accessory 1104 and the device 1106.

There may be other examples of geometric connectors that restrict the connection between the charging accessory 1104 and the device 1106. In one embodiment, the device 1106 may have a geometric pin or rod that lines up with a mechanical button on the charging accessory 1104, such that when the device 1106 is inserted into the charging accessory 1104, the button mechanically retracts insulating flaps that are covering the charging connectors. In another embodiment, rather than a geometric pin or rod, there may be a series of geometric pins. In yet another embodiment, the geometric pin may be shaped like a key that can be coupled with a receiving port in the charging accessory 1104 that unlocks only if the correct shape key is used. This may tie a device 1106 to a particular charging accessory 1104, or alternatively all devices may have identical keys and chargers may have identical ports. In another embodiment, there may be a magnetic component in the device 1106 that retracts the insulating flaps when the device 1106 is inserted into the charging accessory 1104. In another embodiment, there may be a "twist and lock" feature in which the device 1106 may be circular with a geometric pin normal to the circumference. The pin slides down a slot and must be rotated when device is engaged with the charger to retract insulating flaps. Rather than insulating flaps, the charging posts in the charging accessory 1104 may be retracted into the device (e.g. 3-4 millimeters). The embodiments mentioned above may include moving the charging posts towards the device/charger interface to make a connection. In another embodiment, there may be an electric motor that moves the posts into place after the device-charger handshake occurs and is confirmed.

FIG. 20 is a flow chart illustrating the age verification process. In block 2002, a user purchases a device (e.g. device 1106). The device 1106 may include a battery that has a limited amount of charge. The included battery may have only enough charge for one or more puffs. Accordingly, the device 1106 operates until the charge is required, or it operates until a verification is required as in block 2004. The limited amount of charge at purchase will limit the usage before verification. The device could also limit a number of puffs the user can take or limit a cumulative puff duration (e.g. X seconds of puffing) prior to attaching an unlocked charger by utilizing the puff counting software. In other words, the heater is only allowed to be turned on for a limited time (e.g. X cumulative seconds before the device 1106 shuts down or X cumulative time across puffs before the device 1106 shuts down). After the user depletes the battery through vaping, age verification will be required in block 2006. As described above, the age verification through the age verification system 1102 may be through an online connection from a computing device (e.g. smartphone, laptop, tablet, etc.) through which the user verifies their identity and age. In one embodiment, there may be an application (or "app") on a smartphone that provides the connection with the age verification system 1102. The app may include the ability to provide documentation (e.g. driver's license, passport, social security number, etc.) by either photograph, copying, or uploading. In other embodiments, the app may include the age verification system 1102 functionality locally such that the app can verify an age without requiring another network system. In other embodiments, the charging accessory 1104 may have the functionality to verify the user age from the online age verification system 1102. In an alternative embodiment, there may be help desk phone service through which the user calls to verify their age.

The initial age verification (block 2006) may be saved at the age verification system 1102, either at an online resource or locally with an app. As discussed above, each user may be stored in a database that tracks ages that can be referenced for future authentications as in block 2008. Authentication may be referred to as re-verifying the age verification and may not include the same process as the initial age verification. The initial age verification may require certain evidence of the age, whereas subsequent authentication may only require verifying identity and then confirming that identity is of the correct age with the age verification system 1102. As described each future authentication may be required periodically (hourly, daily, weekly, monthly, etc.), may be based on usage (every 100 puffs), may be required each time the user replaces a cartridge, or may be required each time the user charges the device 1106. In block 2010, the charging accessory 1104 can be connected to the device 1106 for charging the device upon authentication. The device 1106 continues to charge in block 2012 and can be used until the next charge is need in block 2014. Upon needing a charge from block 2012, the charger may need to be re-authenticated in block 2008 each time a charge is required. Although not shown, the user may be required to periodically re-verify the age of the user (as in block 2006). For example, the initial age verification may last for one year or another time period.

FIG. 21 is a flow chart illustrating an alternative embodiment of the age verification process. In block 2102, a user purchases a device (e.g. device 1106). In one embodiment, the device may be sold as locked and require the verification and authentication to be unlocked. In block 2104, the purchase process may include an opportunity for the user to verify their age, which is then provided to the age verification system 1102. At the point of sale, the user may be required to verify their age. For example, for a purchase at a store, a store clerk may be required to view the user's identification and then input that information online for storage at the age verification system 1102. Alternatively, at the time of purchase, the user may be required to register the purchase online or with an app. In one embodiment, there may be a kiosk or other mechanism at the time of purchase through which the user can interact to provide a consistent registration process between different retailers. The kiosk may be provided and operated by the owner/operator of the age verification system. For example, this could be incorporated into existing VERIPHONE payment kiosks or be a standalone kiosk that is provided to retailers. The registration process may include providing proof of age. This age verification process may occur at the time of each purchase. In alternative embodiments, the initial age verification may take place once and the user may create a profile (online or with an app) that can be associated with all future purchases that is used for authentication. The device 1106 may operate until a charge is required or until authentication is required in block 2106, which is similar to block 2006. Once the authentication is completed in block 2108, the charger accessory 1104 can be connected to the device 1106 for charging as described with respect to FIG. 20. Cartridges or consumables may be registered as described in U.S. patent application Ser. No. 16/415,444 filed May 17, 2019, filed concurrently and entitled "AGE VERIFICATION WITH REGISTERED CARTRIDGES FOR AN AEROSOL DELIVERY DEVICE," the entire disclosure of which is herein incorporated by reference.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-21 or as otherwise described above may be included in an aerosol delivery device according to the present disclosure.

Many modifications and other implementations of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific implementations disclosed, and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A system comprising:
an age verification system configured to verify an age of a user;
an aerosol delivery device comprising a battery that provides aerosol to the user; and
a charging accessory configured to be connected to an electrical power supply and provide electrical charge to the battery of the aerosol delivery device to electrically charge the battery when the charging accessory is unlocked, wherein the charging accessory is unlocked in response to the user being authenticated with the age verification system;
wherein the charging accessory is initially unlocked in response to the user performing an initial age verification with age verification system by providing evidence of age, and the charging accessory is subsequently unlocked in response to an authentication that comprises a verification of the user's identity without requiring evidence of age.

2. The system of claim 1, wherein the user is authenticated by the charging accessory communicating with the age verification system.

3. The system of claim 2, wherein the charging accessory further comprises authentication circuitry configured for the communication with the age verification system.

4. The system of claim 1, wherein the charging accessory removably couples the electrical power supply with a charging interface of the aerosol delivery device to charge the battery.

5. The system of claim 4, further comprising a host device coupled with the charging accessory, wherein the host device communicate with the age verification system, further wherein the host device comprises the electrical power supply.

6. The system of claim 5, further comprising a network through which the age verification system is coupled with the host device.

7. A charging accessory for an aerosol delivery device comprising:
an electrical power interface that is configured to receive electrical power from an electrical power supply and couple with the aerosol delivery device to provide electrical power to the aerosol delivery device; and
authentication circuitry that is configured to:
receive an age verification of a user;
transition from preventing the electrical power from being provided to the aerosol delivery device to permitting the electrical power to be provided to the aerosol delivery device in response to an initial age verification with evidence of age;
transition to prevent the electrical power from being provided to the aerosol delivery device; and
subsequently transition from preventing the electrical power from being provided to the aerosol delivery device to permitting the electrical power to be provided to the aerosol delivery device in response to a subsequent authentication that comprises a verification of the user's identity without requiring the evidence of age.

8. The charging accessory of claim 7, wherein the authentication circuitry comprises a switch configured to connect a current for the power through the power interface between from the electrical power supply to the aerosol delivery device upon the initial age verification or the subsequent authentication, further wherein the switch does not connect a current for the power through the power interface when the initial age verification or the subsequent authentication fails.

9. The charging accessory of claim 7, wherein the initial age verification comprises an authentication that includes communicating with an age verification system over a network.

10. The charging accessory of claim 9, wherein the authentication is required for each power cycle and references the age verification of the user.

11. The charging accessory of claim 9, wherein an initial age verification operation is performed using identifying documentation such that the authentication that occurs for each power cycle confirms that the user is from the initial age verification operation.

12. The charging accessory of claim 7, wherein the initial age verification comprises an association of a user with an age, such that the subsequent authentication comprises a request to authenticate the association with the user.

13. The charging accessory of claim 12, wherein the initial age verification occurs around a time of purchase and the subsequent authentication occurs during usage.

14. The charging accessory of claim 7, wherein the charging accessory comprises a biometric sensor for the subsequent authentication, wherein the biometric sensor comprises a facial recognition or fingerprint analysis.

15. The charging accessory of claim 7, wherein the facial recognition or the fingerprint analysis for the subsequent authentication compares to data stored from the initial age verification for the user.

16. The charging accessory of claim 7, wherein the charging accessory comprises a charging cable or charging case.

17. The charging accessory of claim 7, wherein the electrical power supply comprises a host device.

18. The charging accessory of claim 17, wherein the host device is configured to communicate with an age verification system over a network regarding the age verification.

19. The charging accessory of claim 17, wherein the host device is configured to communicate with the charging accessory through electric pulses or data pulses.

20. The charging accessory of claim 7, wherein the aerosol delivery device comprises a battery for heating a liquid to generate an aerosol, further wherein the power is provided from the charger accessory to the aerosol delivery device for charging the battery.

21. A method for operating a charging accessory with an age restricted device, the method comprising:
receiving an initial age verification for a user by providing evidence of age;
connecting, in response to the initial age verification, an electric current to the age restricted device;
preventing the electric current from being provided to the age restricted device;
subsequently connecting, in response to the user being authenticated by verifying the user's identity without requiring the evidence of age, an electric current to the age restricted device; and
preventing, when the age verification is not authenticated, the electric current from being provided to the age restricted device when the charging accessory is coupled with the age restricted device.

22. The method of claim 21, further comprising: communicating by the charging accessory with an age verification system for receiving the age verification of the user.

23. The method of claim 22, wherein the age verification comprises information on whether the user has a verified age or not.

\* \* \* \* \*

UNITED STATES PATENT AND TRADEMARK OFFICE
CERTIFICATE OF CORRECTION

| | | |
|---|---|---|
| PATENT NO. | : 11,676,438 B2 | Page 1 of 1 |
| APPLICATION NO. | : 16/415460 | |
| DATED | : June 13, 2023 | |
| INVENTOR(S) | : Sawyer Hubbard et al. | |

It is certified that error appears in the above-identified patent and that said Letters Patent is hereby corrected as shown below:

In the Claims

In Column 39, Claim 1, Line 16, "with age verification system" should read --with the age verification system--

In Column 39, Claim 5, Line 34, "device communicate" should read --device communicates--

Signed and Sealed this
Fifth Day of March, 2024

Katherine Kelly Vidal
*Director of the United States Patent and Trademark Office*